US008292496B1

(12) United States Patent
Fine et al.

(10) Patent No.: US 8,292,496 B1
(45) Date of Patent: Oct. 23, 2012

(54) ENERGETIC MATERIAL DETECTOR

(75) Inventors: David H. Fine, Cocoa Beach, FL (US); Edward E. A. Bromberg, Orlando, FL (US); Sean C. Christiansen, Orlando, FL (US); Steven Bullock, Tehachapi, CA (US); Ravi K. Konduri, Heathrow, FL (US); Geoffrey Solomon, Maitland, FL (US)

(73) Assignee: L-3 Communications CyTerra Corporation, Orlando, FL (US)

( * ) Notice: Subject to any disclaimer, the term of this patent is extended or adjusted under 35 U.S.C. 154(b) by 1142 days.

(21) Appl. No.: 11/940,152

(22) Filed: Nov. 14, 2007

Related U.S. Application Data

(63) Continuation-in-part of application No. 11/460,586, filed on Jul. 27, 2006, now Pat. No. 7,645,069.

(60) Provisional application No. 60/702,616, filed on Jul. 27, 2005, provisional application No. 60/743,083, filed on Dec. 29, 2005, provisional application No. 60/743,402, filed on Mar. 3, 2006, provisional application No. 60/865,771, filed on Nov. 14, 2006.

(51) Int. Cl.
*G01K 25/00* (2006.01)
(52) U.S. Cl. .......................................................... 374/8
(58) Field of Classification Search ................... 374/8
See application file for complete search history.

(56) References Cited

U.S. PATENT DOCUMENTS

| | | | |
|---|---|---|---|
| 2,947,163 A | 8/1960 | Stone | |
| 3,593,563 A | 7/1971 | Marmor et al. | |
| 3,766,635 A | 10/1973 | Cranston | |
| 3,876,999 A | 4/1975 | Lee | |
| 4,023,201 A | 5/1977 | Faulkner | |
| 4,130,016 A | 12/1978 | Walker | |
| 4,166,385 A | 9/1979 | Pate et al. | |
| 4,266,219 A | 5/1981 | Foster et al. | |
| 4,466,943 A | 8/1984 | Murase et al. | |
| 4,533,258 A | 8/1985 | Milovidov | |
| 4,639,605 A | 1/1987 | Seki et al. | |
| 4,670,404 A | 6/1987 | Swift et al. | |
| 4,926,356 A * | 5/1990 | Kucera et al. ................. | 702/136 |
| 5,121,101 A | 6/1992 | Jakubowski et al. | |
| 5,163,753 A | 11/1992 | Whiting et al. | |

(Continued)

FOREIGN PATENT DOCUMENTS

GB          2191477 A          12/1987

(Continued)

OTHER PUBLICATIONS

International Search Report and the Written Opinion of the International Searching Authority issued in International Application No. PCT/US06/29301 on Jul. 18, 2008.

(Continued)

*Primary Examiner* — Lisa Caputo
*Assistant Examiner* — Jamel Williams
(74) *Attorney, Agent, or Firm* — Fish & Richardson P.C.

(57) ABSTRACT

In one general aspect, a sample area is energized. A thermal energy status of the sample area is monitored. The thermal energy status including at least one of a radiant energy and a temperature. A thermal signature of a region included in the sample area is determined based on the thermal energy status of the region. The thermal signature is analyzed to determine whether explosive particles are included in the region.

34 Claims, 24 Drawing Sheets

U.S. PATENT DOCUMENTS

| | | | |
|---|---|---|---|
| 5,165,792 | A | 11/1992 | Crowe et al. |
| 5,346,306 | A | 9/1994 | Reading et al. |
| 5,364,795 | A | 11/1994 | Sausa et al. |
| 5,457,639 | A | 10/1995 | Ulich et al. |
| 5,473,162 | A | 12/1995 | Busch et al. |
| 5,552,257 | A | 9/1996 | Stewart et al. |
| 5,638,166 | A | 6/1997 | Funsten et al. |
| 5,759,859 | A | 6/1998 | Sausa |
| 5,760,898 | A * | 6/1998 | Haley et al. .................. 356/318 |
| 5,905,571 | A | 5/1999 | Butler et al. |
| 5,918,263 | A * | 6/1999 | Thundat ....................... 73/35.16 |
| 5,932,796 | A | 8/1999 | Arthaud et al. |
| 6,245,576 | B1 * | 6/2001 | Hiley ............................ 436/110 |
| 6,309,591 | B1 | 10/2001 | Yoo et al. |
| 6,355,930 | B1 | 3/2002 | Sivathanu et al. |
| 6,406,918 | B1 * | 6/2002 | Bannister et al. ............. 436/155 |
| 6,556,650 | B2 | 4/2003 | Francke |
| 6,613,207 | B1 * | 9/2003 | De La Prieta et al. ........ 204/426 |
| 6,623,976 | B1 | 9/2003 | Hale et al. |
| 6,649,416 | B1 | 11/2003 | Kauer et al. |
| 6,654,443 | B1 | 11/2003 | Hoffman |
| 6,773,674 | B2 * | 8/2004 | Bannister et al. ............... 422/83 |
| 6,803,577 | B2 | 10/2004 | Edner et al. |
| 6,872,786 | B2 | 3/2005 | Murray et al. |
| 6,946,300 | B2 | 9/2005 | Nguyen et al. |
| 6,984,524 | B2 | 1/2006 | Nguyen et al. |
| 7,006,857 | B2 | 2/2006 | Braig et al. |
| 7,088,435 | B2 | 8/2006 | Brestel et al. |
| 7,116,798 | B1 | 10/2006 | Chawla |
| 7,348,562 | B2 | 3/2008 | Irani |
| 7,449,695 | B2 | 11/2008 | Zimdars et al. |
| 7,538,326 | B2 | 5/2009 | Johnson et al. |
| 7,645,069 | B1 * | 1/2010 | Fine et al. ......................... 374/8 |
| 7,666,356 | B2 | 2/2010 | O Donnell et al. |
| 7,694,346 | B2 | 4/2010 | Adams et al. |
| 7,833,802 | B2 | 11/2010 | Henry et al. |
| 7,939,803 | B2 | 5/2011 | Moore |
| 8,101,915 | B2 | 1/2012 | McGill et al. |
| 2002/0008523 | A1 | 1/2002 | Klang |
| 2003/0031915 | A1 | 2/2003 | Diez et al. |
| 2003/0207271 | A1 | 11/2003 | Holwitt et al. |
| 2004/0014233 | A1 * | 1/2004 | Bannister et al. ............. 436/155 |
| 2004/0053421 | A1 | 3/2004 | Nguyen et al. |
| 2004/0060625 | A1 | 4/2004 | Barbee et al. |
| 2004/0067302 | A1 | 4/2004 | Burberry |
| 2004/0185156 | A1 | 9/2004 | Garwood |
| 2004/0194548 | A1 | 10/2004 | Dayagi |
| 2005/0008063 | A1 | 1/2005 | Chippett |
| 2005/0078732 | A1 | 4/2005 | de Ris et al. |
| 2005/0176391 | A1 | 8/2005 | Butters |
| 2005/0220265 | A1 | 10/2005 | Besson |
| 2005/0275582 | A1 | 12/2005 | Mohan |
| 2006/0191320 | A1 | 8/2006 | Pinnaduwage |
| 2006/0289772 | A1 | 12/2006 | Johnson et al. |
| 2007/0085998 | A1 | 4/2007 | Brestel et al. |
| 2007/0086925 | A1 | 4/2007 | O'Donnell et al. |
| 2008/0060455 | A1 | 3/2008 | Coyle |
| 2008/0100836 | A1 | 5/2008 | Hagler |
| 2009/0044641 | A1 | 2/2009 | Konduri et al. |
| 2010/0025582 | A1 | 2/2010 | Weil |
| 2010/0253935 | A1 | 10/2010 | Mackinnon et al. |
| 2011/0151575 | A1 | 6/2011 | Fraser et al. |
| 2011/0151675 | A1 | 6/2011 | Frank et al. |
| 2011/0282799 | A1 | 11/2011 | Huston |

FOREIGN PATENT DOCUMENTS

| | | |
|---|---|---|
| JP | 03118458 A | 12/1987 |
| JP | 04062460 A | 2/1992 |
| JP | 8145921 A | 6/1996 |
| JP | 2000035371 A | 2/2000 |
| JP | 2001249095 A | 9/2001 |
| WO | WO9714033 A1 | 4/1997 |

OTHER PUBLICATIONS

PCT International Preliminary Report on Patentability issued in International Application No. PCT/US2006/029301 mailed Sep. 4, 2008.

Office Action for U.S. Appl. No. 12/685,412, mailed Mar. 30, 2012, 13 pages.

English translation of Examination Report for corresponding Japanese Application No. 2008-533340, mailed Oct. 12, 2011, 3 pages.

Examination Report, with English translation, for corresponding Israel Application No. 189,005, mailed Sep. 4, 2011, 4 pages.

J. Powling et al., "Measurement of the Burning Surface Temperatures of Propellant Compositions by Infra-red Emission," Combustion and Flame, Elsevier Science Publishing Co., Inc., New York, NY; US LNKD-DOI:10.1016/0010-2180(62)90087-1, vol. 6, Jan. 1, 1962, pp. 173-181, XP025806190 ISSN: 0010-2180.

Viviane Bouyer et al., "Shock-to-detonation transition of nitromethane: Time-resolved emission spectroscopy measurements," Combustion and Flame, Elsevier Science Publishing Co., Inc., New York, NY; US LNKD-DOI:10.1016/J. Combustflame. 2005.07.004, vol. 144, No. 1-2, Jan. 1, 2006, pp. 139-150, XP025059529 ISSN: 0010-2180.

Office Action for U.S. Appl. No. 12/685,412, mailed Aug. 12, 2011, 12 pages.

David H. Fine, "Spontaneous Ignition and Thermal Explosions," Sep. 1, 1967, Dissertation submitted in partial fulfillment of the requirement for the Degree of Doctor of Philosophy at the University of Leeds.

* cited by examiner

ENERGETIC MATERIAL DETECTOR

CROSS-REFERENCE

This application is a continuation-in-part of U.S. application Ser. No. 11/460,586, filed Jul. 27, 2006, and titled ENERGETIC MATERIAL DETECTOR, which claims priority from U.S. Provisional Application Nos. 60/702,616, filed Jul. 27, 2005, and titled TRACE EXPLOSIVES DETECTOR BASED UPON DETECTING EXOTHERMIC DECOMPOSITION, and 60/743,083, filed Dec. 29, 2005, and titled ENERGETIC MATERIAL DETECTOR FOR EXPLOSIVE TRACE DETECTION; and 60/743,402, filed Mar. 3, 2006, and titled ENERGETIC MATERIAL DETECTOR FOR EXPLOSIVE TRACE DETECTION. This application also claims priority to U.S. Provisional Application No. 60/865,771, filed Nov. 14, 2006, and titled ENERGETIC MATERIAL DETECTOR. Each of these applications is incorporated by reference.

TECHNICAL FIELD

This disclosure relates to detecting energetic materials, such as explosives.

BACKGROUND

Particles may be analyzed for their thermodynamic properties to determine if the particles are energetic (e.g., if the particles are particles of explosive materials).

SUMMARY

In one general aspect, a sample area is energized. A thermal energy status of the sample area is monitored. The thermal energy status including at least one of a radiant energy and a temperature. A thermal signature of a region included in the sample area is determined based on the thermal energy status of the region. The thermal signature is analyzed to determine whether explosive particles are included in the region.

Implementations may include one or more of the following features. The thermal signature may include an increase in the thermal energy status during a first time period and a decrease in the thermal energy status during a second time period. Determining whether explosive particles are included in the region may include determining whether the thermal signature includes the increase in the thermal energy status over the first time period and the decrease in the thermal energy status over the second time period. The first time period may occur before the second time period. Determining the thermal signature of a region included in the sample area may include determining the time rate of change of the thermal energy status of the region.

Determining the thermal signature of a region included in the sample area also may include determining the average monitored thermal energy status of the sample area at a time, and subtracting the average monitored thermal energy status at the time from the thermal energy status of the region before determining the time rate of change of the thermal energy status of the region.

Monitoring a thermal energy status of the sample area may include monitoring the sample area with a thermal detector and detecting radiant energy released from the sample area. A region included in the sample area may include a region imaged by a pixel of the thermal detector.

Analyzing the thermal signature to determine whether explosive particles are included in the region may include determining that explosive particles are included in the region. One or more characteristics of the thermal signature may be determined. At least one of the one or more characteristics of the thermal signature to characteristics may be compared of known thermal signatures. The thermal signature may be classified based on the comparison after detecting the material is an explosive. Determining one or more characteristics of the thermal signature may include analyzing the thermal signature to determine a heat of decomposition of the explosive materials. Determining one or more characteristics of the thermal signature may include analyzing the thermal signature to determine an activation energy of the explosive materials.

Classifying the thermal signature based on the comparison may include identifying the one or more explosive materials as a particular explosive. Classifying the thermal signature based on the comparison may include identifying the one or more explosive material as belonging to a class of explosive materials. Energizing a sample area may include supplying energy such that an exothermic decomposition of particles included in the sample area is triggered.

Based on the analyzed thermal signature, it may be determined that one or more explosive materials are included in the sample area. The thermal signature may be compared to known thermal signatures after determining that the samples include energetic materials. Whether the known thermal signatures includes the thermal signature may be determined. If a determination is made that the known thermal signatures do not include the thermal signature, the thermal signature may be stored as one of the known thermal signatures.

Monitoring a thermal energy status of the sample area may include monitoring at least one of radiant energy or temperature released from exothermic decomposition of particles. Energizing the sample area may include resistively heating the sample area and applying a current through a conductive collection material. Applying a current through a conductive collection material includes applying a current through a metal mesh. Applying a current through a conductive collection material includes applying one or more of a step current and a ramp current. Energizing the sample media includes radiatively heating the sample area. Radiatively heating the sample area includes radiatively heating the sample area from a distance outside an area adjacent to the device used to radiatively heat the sample area.

Analyzing the thermal signature to determine whether explosive particles are included in the region may include determining one or more characteristics of the thermal signature. At least one of the one or more characteristics of the thermal signature may be compared to characteristics of known thermal signatures. The thermal signature may be classified based on the comparison.

In another general aspect, a system includes a sample energizer configured to energize a sample area, and a sensor configured to monitor a thermal energy status of the sample area. The thermal energy status includes at least one of a radiant energy and a temperature. The system also includes an analyzing device configured to determine a time-dependent thermal signature of a region included in the sample area based on the monitored thermal energy status. The analyzing device is also configured to determine the presence of the explosive materials based on characteristics of the time-dependent thermal signature.

The time-dependent thermal signature may include an increase in the thermal energy status during a first time period and a decrease in the thermal energy status during a second time period. The analyzing device may be configured to determine the presence of explosive materials based on characteristics of the time-dependent thermal signature by determining whether the thermal signature includes the increase in the thermal energy status over the first time period and the decrease in the thermal energy status over the second time period. Determining the time-dependent thermal signature of a region included in the sample area may include determining the time rate of change of the thermal energy status of the region.

The analyzing device also may be configured to determine, based on the analyzed thermal signature, that one or more explosive materials are included in the sample area and to determine one or more characteristics of the thermal signature. The analyzing device also may compare characteristics of the thermal signature to a library of characteristics of known thermal signatures and classify the thermal signature based on the comparison.

In another general aspect, a computer program product tangibly embodied on a computer-readable medium includes instructions that, when executed, cause a thermal signature analysis component to perform operations including energizing a sample area and monitoring a thermal energy status of the sample area. The thermal energy status includes at least one of a radiant energy and a temperature. The instructions also cause the thermal signature analysis component to determine a thermal signature of a region included in the sample area based on the thermal energy status of the region and analyze the thermal signature to determine whether explosive particles are included in the region.

The thermal signature may include an increase in the thermal energy status during a first time period and a decrease in the thermal energy status during a second time period, and the computer program product may include instructions that, when executed, cause the thermal signature analyzing component to determine the presence of explosive materials based on characteristics of the thermal signature by determining whether the thermal signature includes the increase in the thermal energy status over the first time period and the decrease in the thermal energy status over the second time period.

In another general aspect, a sample area is energized. A thermal energy status of the sample area is monitored, the thermal energy status including at least one of a radiant energy and a temperature. A thermal signature of a region included in the sample area is determined based on the thermal energy status of the region. The thermal signature is analyzed to determine whether the thermal signature includes an exotherm that occurs before an endotherm. Whether the region includes one or more particles of explosive materials is determined based only on determining that the thermal signature includes an exotherm that occurs before an endotherm.

Implementations of any of the techniques described above may include a method, a process, a system, or instructions stored on a computer-readable medium.

The details of one or more implementations are set forth in the accompanying drawings and the description below. Other features will be apparent from the description and drawings, and from the claims.

DESCRIPTION OF DRAWINGS

Like reference symbols in the various drawings indicate like elements.

DETAILED DESCRIPTION

Figure 1:
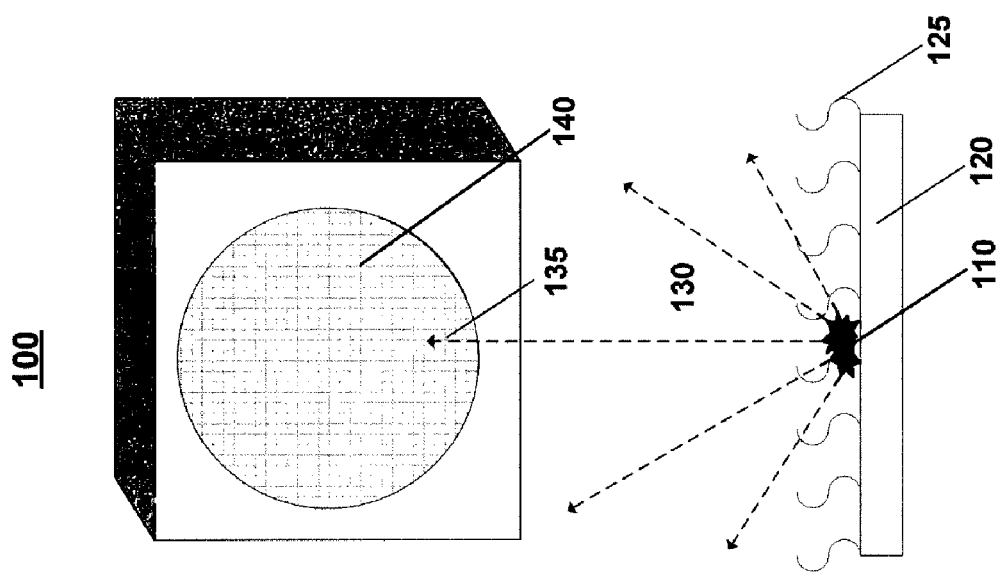
FIG. 1 illustrates a decomposition system.

Individuals have been able to conceal explosives by using unusual materials or precautionary methods to thwart detection. For example, while a traditional weapon, such as a grenade, may be detected on a person by means of a metal detector or in luggage by means of an x-ray scanner, explosives, such as, C-4 and TNT, may not be detected by such methods.

Also, conventional explosive detection equipment designed to detect certain known explosive material with specific chemical structures generally does not detect non-standard or home-made explosives.

In order to screen a wider variety of potentially threatening material, trace sampling of particles may be used. Specifically, a sample of trace (e.g., microscopic) particles may be collected from an item or individual, and analyzed for properties indicative of explosives or threats. The analysis of particles may be conducted using a variety of mechanisms, such as an ion mobility detector (IMS), gas chromatography coupled with a chemiluminescence detector (GC-CL), or mass spectrometry. Many techniques are able to detect only specific chemicals, or chemicals with very specific types of chemical structures.

Whether a particle is an explosive may be determined by heating the particle and monitoring the time-dependent thermal signature produced by the particle as the particle is heated. Heating particles that are explosives triggers an exothermal decomposition (e.g., an explosion or a thermal decomposition) of the particle, whereas heating particles that are not explosives does not trigger a thermal decomposition. Heating particles results in the particles increasing in temperature or increasing the amount of radiant energy released by the particle. In general, an explosive particle has a time-dependent thermal signature that includes an exotherm and an endotherm. The exotherm occurs when the particle releases heat during the exothermal decomposition (e.g., as the particle explodes). The endotherm occurs when the explosion has consumed the explosive particles, thus ending the explosion, and the area where the explosive particle was located cools down to the temperature of the surrounding area. In contrast, the time-dependent thermal signatures of non-explosive particles generally do not include an exotherm and an endotherm. Instead, the temperature of the non-explosive particles or the radiant energy released from the particle increases monotonically (e.g., the temperature or radiant energy increases or remains the same) as heat is applied to the particle.

Accordingly, particles that are explosives may be distinguished from particles that are non-explosives by heating the particles, monitoring the particles over time to determine the time-dependent thermal signature of the particle, and determining whether the signature includes an endotherm and an exotherm. Because the presence of an endotherm and an exotherm is an almost universal trait of thermal signatures of explosives, analyzing the thermal signatures for the presence of an endotherm and an exotherm allows a determination of whether an explosive is present without any additional knowledge of the characteristics of the thermal signatures or the particles. For example, analyzing the thermal signature to determine if the signature includes an endotherm and an exotherm allows a determination of whether an explosive is present without the use of a library of predefined thermal signatures. Thus, such techniques may be used to detect the presence of explosives that have not been encountered by the detection system before, such as homemade explosives, explosives that are contaminated with other substances, or other non-standard explosives.

As the particles are heated, the particles may be monitored with, for example, an infrared detector that detects radiant energy (which also may be referred to as thermal energy) released from the particle as it is heated. The time-dependent thermal signature may be based on a temperature that the detector derives from the detected radiant energy. In general, the temperatures is derived from the detected radiant energy based on a predefined calibration performed by the detector. Alternatively or additionally, the time-dependent thermal signature of the particle may be based on the radiant energy that is directly measured by the detector. By avoiding the conversion between radiant energy and temperature, some implementations that use the directly measured radiant energy may have more accurate results and may be implemented more efficiently.

Various methods, such as resistive, conductive, radiative, or laser heating, may be used to heat the particle. Resistive heating may be appropriate for systems where particles are collected and analyzed at close range. For example, a swipe or vacuum collection system may deposit particles on a steel mesh, which may be directly resistively heated. For long-range systems, radiative heating may be appropriate. For example, a radiative heater may be incorporated into an x-ray baggage scanner and may be used to detect explosive or other energetic particles from a range of less than a meter. In another example, the radiative heater may be used to heat the surface of an automobile to determine whether there are energetic particles on the surface of the automobile. Other systems may be radiatively heated and detected from much larger ranges, such as, for example, tens or hundreds of meters.

Referring to FIG. 1, a detection system 100 analyzes a sample 110 using a collection material 120 and an infrared (IR) sensor 140. In the system 100, the sample 110 is placed on the collection material 120 and then heated 125 to trigger thermal decomposition. Energy 130 is released from the sample 110 during decomposition, and a portion 135 of that energy is detected by the IR sensor 140 to infer the presence of explosive particles.

The sample 110 may be collected from a variety of sources and by means of a variety of methods. In general, people who handle or work with explosives or other materials typically become contaminated with trace residue of the materials. For example, explosive particles may remain on the hands following manufacturing and/or handling of a bomb or explosive material, and some of these particles are may be transferred to the person's clothing. Such trace residue may also be transferred to items such as wallets, spectacles, keys, purses, and door handles, and these items may serve to re-contaminate the hands, even when they are washed and the individual changes clothing. The body, clothes, or articles may be swabbed by a collection device or vacuumed onto the collection material 120 to collect the trace residue as the sample 110 for analysis.

The collection material 120 may be constructed out of a variety of materials, such as, for example, Teflon, a stainless steel mesh, woven carbon fibers, a deactivated glass wool pad, a nichrome wire or ribbon, aluminum (and or stainless steel or nickel or other metals) coated polyimide, or carbon filled polyimide. If resistive heating is being employed, the collection material 120 may need to be conductive. If radiative heating is being employed, conductivity of the collection material 120 is not required.

Triggering thermal decomposition of the sample relies on the rapid kinetics and thermodynamics associated with the thermal decomposition of explosives. Although most molecules decompose endothermically when heated in an atmosphere deprived of oxygen, an explosive compound decomposes exothermically and releases heat to the environment. The released heat is immediately transferred to the molecules surrounding the decomposing explosives, which results in a localized increase in temperature, thus increasing the radiant energy given off at that localized area. The radiant energy produced at that localized area is monitored by the detector and provides a measurable indicator of the presence and/or type of an explosive sample 110.

Specifically, explosive samples 110 decompose exothermically (they release heat to the surroundings) when heated anaerobically. If the mass of the explosives is large enough, the temperature rises, which accelerates the reaction rate even further, releasing additional heat, and culminating in a runaway thermal explosion. For sub-critical masses, the material is consumed before it explodes as heat is lost to the surroundings. Nevertheless, even for these sub-critical cases, the temperature rises above its surroundings before decaying back to the ambient.

The IR sensor 140 senses the portion 135 of the thermal energy (which also may be referred to as radiant energy) 130 released during decomposition, which enables detection of explosives, including nitro-organics and nitro-salts, peroxides, perchlorates, and gun powder, as well as homemade explosives of as yet unknown composition. The IR sensor 140 employs an IR detection array to detect the thermal signature of the decomposition. In one implementation, the IR detection array is configured to detect heat in the mid-wave IR (MWIR), 3 to 5 micron wavelength, 5 to 8 micron wavelength, or long-wave IR (LWIR), 8 to 12 micron wavelength, regions to observe the temperature of the environment surrounding an explosive particle. Thermal imaging sensors employing detection in the MWIR region benefit from superior resolution and contrast while those detecting in the LWIR region offer enhanced sensitivity to smaller temperature fluctuations and are less affected by atmospheric conditions (e.g., LWIR radiation can be transmitted through mist and smoke).

For trace explosive decomposition, the inherently small particle sizes complicate the detection process. For an explosive compound undergoing anaerobic thermal decomposition, the heat released is expected to be equivalent to about a 100° C. temperature rise in a 200° C. environment within a five to five hundred millisecond time frame, depending upon the type of explosive, its mass, the heating rate and the rate of heat loss. In some cases, the time frame is 5 to 30 milliseconds. If all of the exothermic energy produced by the decomposition of the explosive occupied one instantaneous field of view (IFOV) of the IR detection array, this would be easily detectable, since most MWIR/LWIR sensors have sensitivities near 0.05° C. However, trace amounts of explosive particles emitting this heat may weigh as little as a few nanograms and their emitted energy may only occupy a region 0.1 to 0.01 millimeters in diameter. Since the IFOV per pixel of a typical sensor lens is about two millimeters in diameter at close range (approximately one foot away from the source), the released energy from a trace explosive is undetectable across the IFOV area. In this case, the temperature rise has been diluted across the entire IFOV and appears as a temperature increase as small as 0.003° C. for a nanogram-size particle.

In one implementation, in order to detect localized heat signatures, an IR detection array is appropriately configured to record fast, microscopic reactions. Because of these constraints, the IR sensor 140 has a macro (close-up) lens capable of achieving an IFOV of between 50 and 150 microns in diameter per pixel. In addition, the resolution of the IR sensor 140 is sufficient to provide numerous individual pixels which act as their own individual heat detectors and serve to increase the sensitivity of the detection of energetic particles. For example, doubling the resolution of the IR sensor 140 leads to a four to eight time reduction of the lower detection limit. If the IR sensor 140 integration time between frames is long relative to the energy release, the energy is time averaged and may not be captured by the sensor. For example, for a five to ten millisecond reaction and using a 60 Hz (16 ms) imaging rate, the observed energy released from an energetic particle is reduced by less than a factor of 3.

In one implementation, the IR sensor 140 includes a long wave infrared detector (LWIR) that is sensitive in the 7.5 to 14 micron range. The detector is equipped with a focusing lens in order to resolve pixels down to about 50 microns. The refresh rate of the system is 60 Hz. The detector is a 320×240 array with 76,800 pixels. The sensitivity of each pixel is specified as 0.05° C., which facilitates sensitivity at the single digit nanogram level or better. Since the particle mass is inversely proportional to the third power of the pixel size, the sensitivity can be enhanced by using a more powerful focusing lens.

The previous description provides an exemplary implementation of a decomposition system. Other implementations may include other or different features. For instance, the collection material 120 may be an individual sample which is clamped down for heating.

Figure 2:
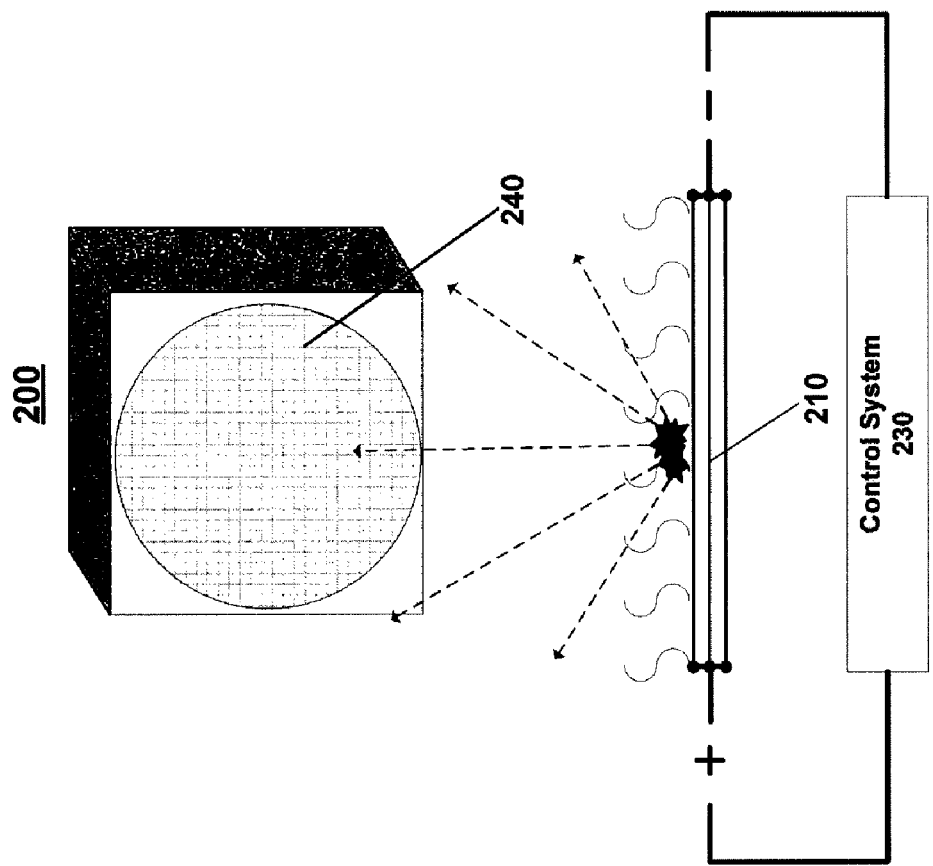
FIG. 2 illustrates a detection system employing resistive heating.

Referring to FIG. 2, a detection system 200 employing resistive heating includes a conductive collection material 210, a control system 230 and an IR sensor 240. In the system 200, an electrical current is run through the collection material 210, which heats due to inherent resistance and triggers energetic decomposition of the sample.

The control system 220 directs the flow and duration of current through the conductor 210. Depending on implementation, varying types of current signals may be produced by the control system 220. A step current may be used to quickly adjust the current to a desired level and is useful in triggering all explosive materials to decompose quickly with minimal oxidation in an atmosphere.

In other implementations, a ramp current that increases at a constant rate is used. Since thermal decomposition is triggered at differing energy levels for differing explosive materials, ramped current enables the system 200 to more precisely determine the nature of the explosive. Other currents shapes, such as, for example, plateaus, may be included to determine further characteristics of the sample.

A rapid heating rate facilitates near anaerobic heating conditions, as oxygen requires time to reach the reaction site. In particular, when heating a sample in an atmosphere with ambient oxygen (e.g., air), rapid heating (e.g., 300° C. to 400° C./second), such as the heating produced by a step current, is desirable to avoid combustion or oxidation of non-explosive particles. When heated slowly enough to allow oxygen to reach the reaction site (e.g., a few seconds), contaminants, such as diesel fuel or sugar, may combust or oxidize. Since explosive materials include the required oxygen for combustion within their chemical structure or mixture, thermal decomposition is generally triggered before any combustion with ambient air, during rapid heating.

In one particular implementation, the conductive collection material 210 is a 400 mesh, 316 grade stainless steel, which includes an opening that is 38 microns between wires. The mesh is heated electrically using a power supply operating at 4.5 volts and approximately 22 amps while an IR sensor is focused onto the mesh using a 0.5× macro germanium lens with a nominal resolution limit of 90 microns per pixel. The data is collected at 60 frames per second via a Firewire connection between the IR detector and the data collection electronics.

The previous description provides an exemplary implementation of a decomposition system employing resistive heating. Other implementations may include other or different features. For instance, the conductive collection material 210 may be replaced with a heat resistant collection material attached to a conductor. Also, heating sensing devices connected to the control system may detect the heat level. The detected heat level may be used to generate a feedback loop with the control system.

Figure 3:
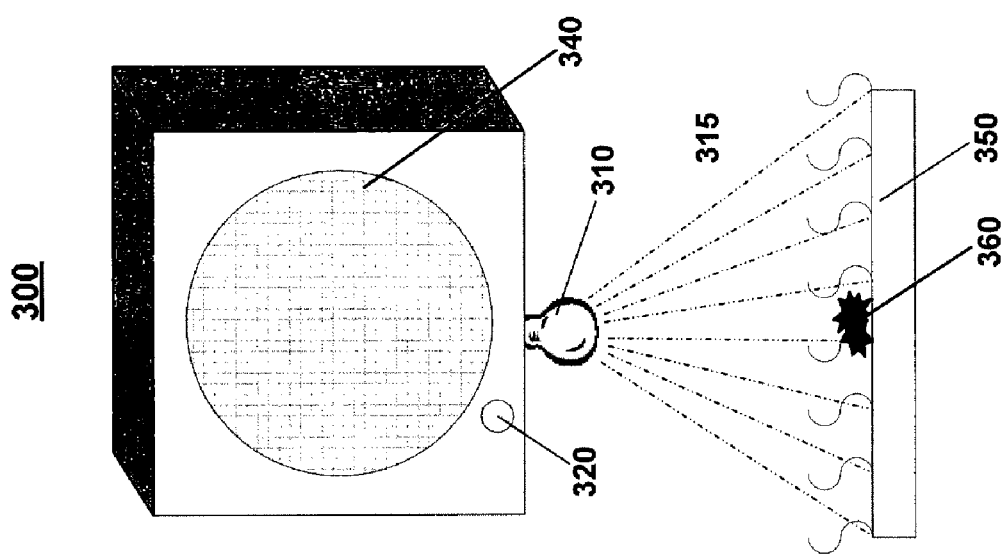
FIG. 3 illustrates a detection system employing radiative heating.

Referring to FIG. 3, a detection system 300 employing radiative heating includes a radiation device 310, a pyrometer 320, an IR sensor 340 and a sample medium 350 that carries a sample 360. In the system 300, radiation 315 is directed to the sample medium 350. Struck by the radiation, the sample medium 350 heats and thermal decomposition of sample 360 is triggered. The radiative source may be on either side of sample media 350. If the source is on the far side then the sample media 350 should be to be thin to allow for rapid transfer of the radiative heat to the sample 360. For example, the sample media 350 is about 0.2 millimeters thin.

The intensity or duration of the emitted radiation 315 by the radiation device 310 may be based upon measurement of the pyrometer 320, which measures the rapid heating of the sample 360 in real-time. The detector itself may serve a dual purpose and be used to measure the surface temperature and thus and can replace the stand-alone pyrometer. In one implementation, the radiation device 310 is a flash-lamp, which may rapidly release enough energy to trigger thermal decomposition. By varying the power level and material used, flash-lamp implementations may be used to flash objects at several meters. If an infrared laser, such as a q-switched niobium YAG system, is used to heat the sample 360, the heating may be conducted over great distances (10-100s of meters).

The previous description provides an exemplary implementation of a decomposition system employing radiative heating. Other implementations may include other or different features. For instance, the radiative system may be designed to release set amounts of energy without requiring a pyrometer for control.

Figure 4:
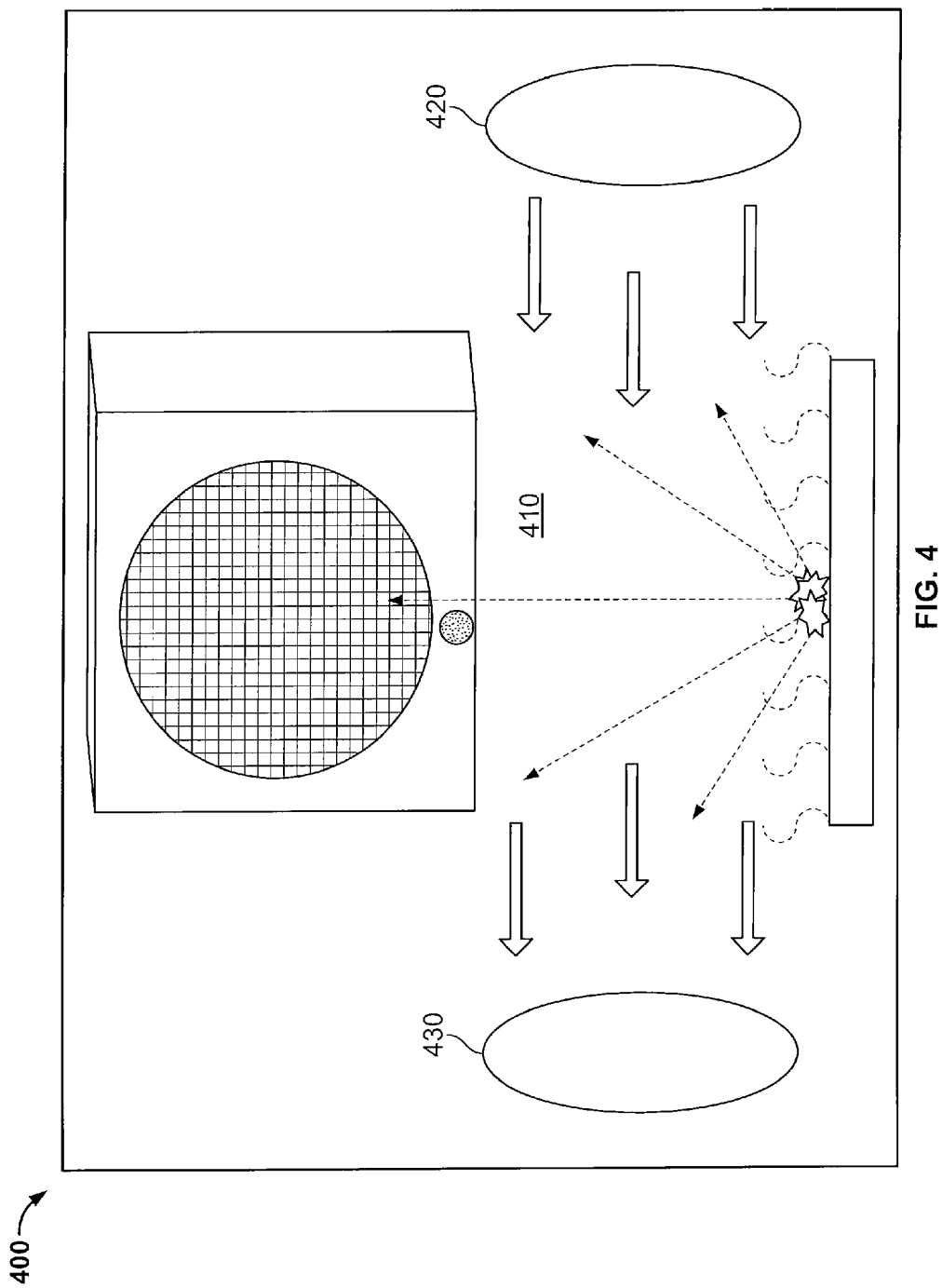
FIG. 4 illustrates a detection chamber employing atmospheric alteration.

Referring to FIG. 4, a detection chamber 400 employing atmospheric alteration, includes an input vent 420 and an output vent 430 to generate an altered atmosphere 410 in the chamber 400 by reducing air-pressure, introducing non-reactive gases, or both. The altered atmosphere 410 features less ambient oxygen available for combustion or oxidation with contaminants.

The input vent 420 is optional, and introduces non-reactive gases, such as, for example, nitrogen or neon, into the atmosphere. The non-reactive gases decrease the availability of gaseous oxygen for combustion or oxidation. The output vent 430 removes gas to lower pressure, and, consequently, lower the amount of gaseous oxygen in the chamber 400. By employing the input and output vents 420 and 430, the chances of contamination are lowered, and heating to trigger thermal decomposition may be slowed to levels that would create combustion in air. The chamber 400 may be particularly useful in implementations employing a slow ramp or plateau style of heating.

The previous description provides an exemplary implementation of a decomposition chamber employing atmospheric alteration. Other implementations may include other or different features. For instance, the chamber may be designed to simply remove the atmosphere without requiring an input vent.

Figure 5:
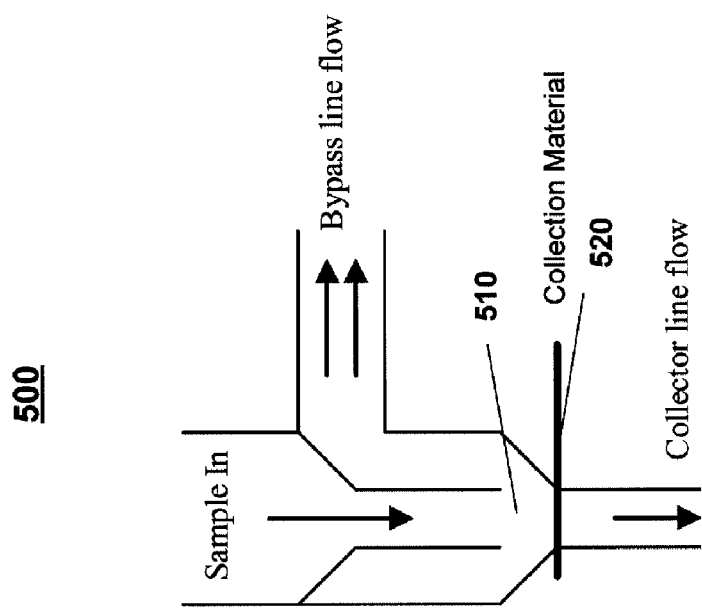
FIG. 5 illustrates an impact collector.

Referring to FIG. 5, an impact collector 500 may be used to deposit one or more air streams of vacuumed samples including explosive particles onto a collection material 520 which may be analyzed as described in the decomposition system 100 with respect to FIG. 1. The air steams may be generated by vacuuming an object, such as clothing, luggage, or an individual's skin, that is to be tested. In the impact collector 500, there is a critical flow to avoid particles falling out of the airflow and onto the tubing walls. One implication of particles falling out of the sample stream is a loss of sample that leads to a false negative. Another implication is one of carry over. Specifically, if a particle falls out of the sample stream, the particle has the potential of showing up in later samples leading to a false positive. Because of such implications, after every positive sampling, there may be a clearing purge cycle, where the system is run without additional sample material.

In the impact collector 500, the air and explosive vapors divide according to the ratio of the bypass flow to the collector flow. Typical collector flows are between 0 and 10 percent of the total flow. Particles, however, are not able to make the 180° turn 510 and thus impact upon the collection material 520. In order to keep the piping of the turnstile clean, valves may be placed downstream of the collection system and kept closed except during the sampling time.

In one particular implementation, the internal inner-diameter of the impact collector 500 is about 1.5 cm. The outer ring is about 3 cm in diameter. If the collection material 520 rotates, the impact collector 500 itself needs to clear the collection material 520. The impact collector 500 may need to seal against the portion of the collection material 520 at the outer ring with the inner tube being from about 0.2-2.0 cm away from the collection material 520. An O-ring may be included on the outer tube to form a seal. In come cases, slight leakage may be acceptable. Depending on implementation, either the impact collector 500 is lowered to form the seal, or the collection material 520 itself is raised to form the seal. Once the deposition has occurred, the collection material 520 or a portion of the collection material 520 may be heated to trigger decomposition.

Figure 6A:
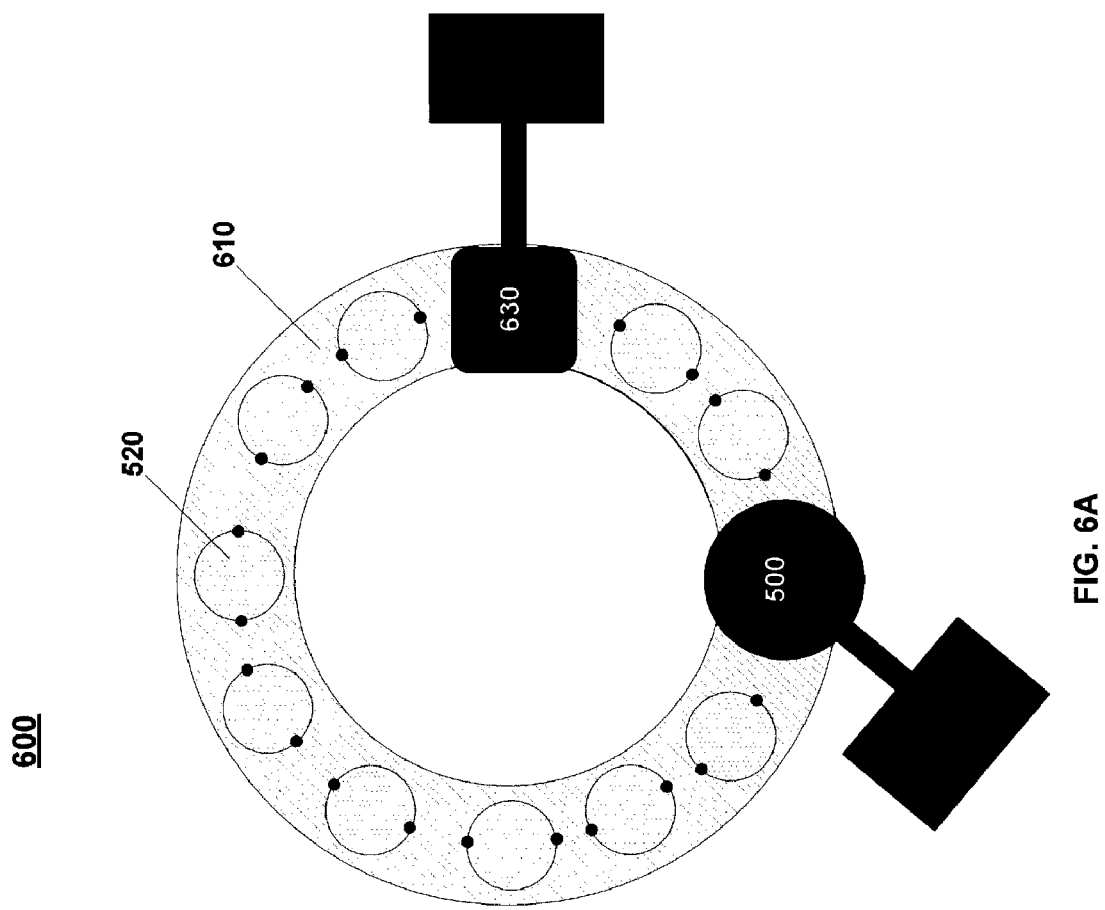
FIGS. 6A and 6B illustrate a top and side view of a collection and detection system.

Referring to FIG. 6A, a top view of a collection and detection system 600 includes the impact collector 500 and collection material 520 of FIG. 5, and a decomposition and analysis system 630. The decomposition system 630 may be any of the systems 100-400 of FIGS. 1-4. In the collection and detection system 600, the impact collector 500 is used to deposit the sample onto the collection material 520. A media moving mechanism 660 (FIG. 6B) moves the collection material 520, which is mounted on a carousel wheel 610, such that the collection material 520, including the sample, moves from a region adjacent to the impact collector to a region within the decomposition and analysis system 630. The deposited material is than analyzed for traces of a specific material.

Figure 6B:
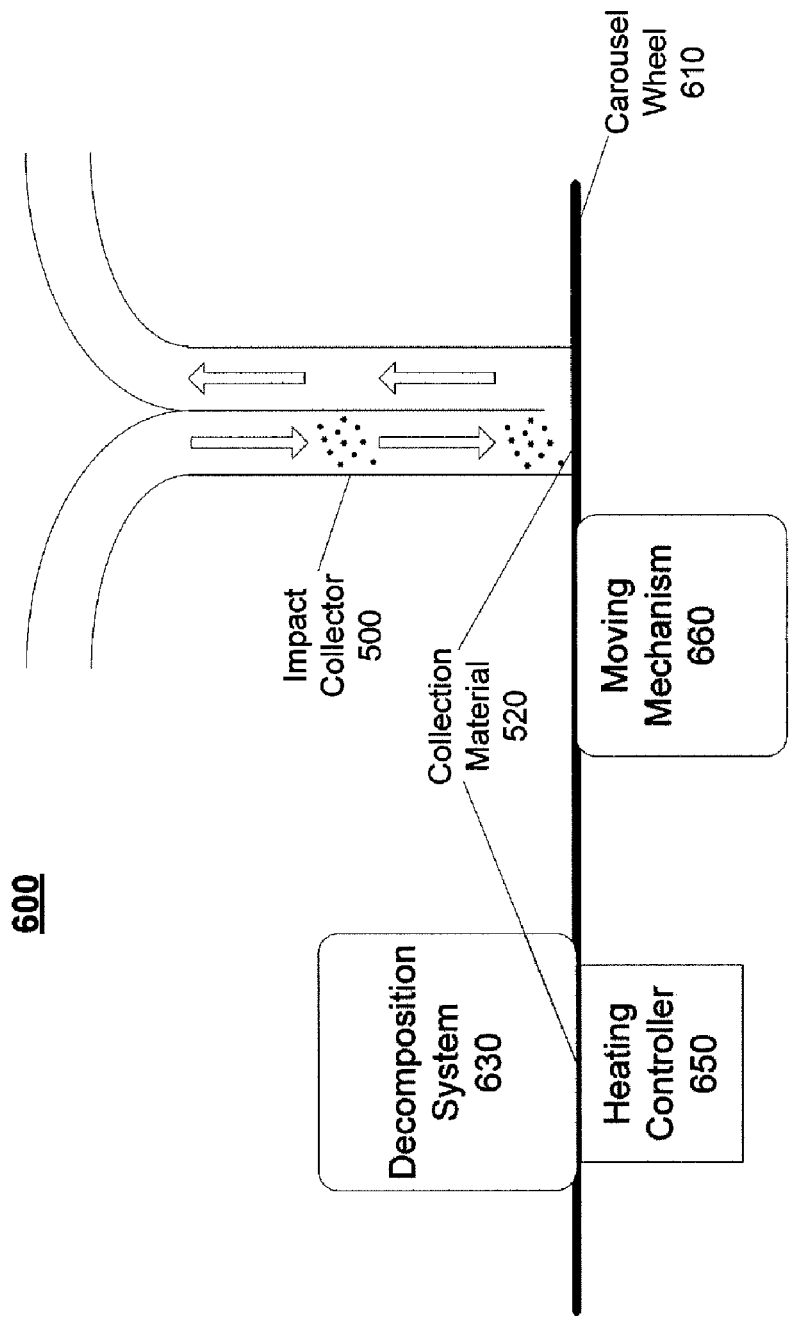

Referring to FIG. 6B, a side view of a collection and detection system 600 includes a heating controller 650 and the media moving mechanism 660. The discussion below refers to two specific implementations directed to resistive and radiative heating to cause exothermic decomposition, but other methods of initiating thermal decomposition may also be used. In particular, elevating the temperature of a particle by using electromagnetic radiation, lasers, the convection of heat via warm air to the particle, or the conduction of heat to the particle would be sufficient for causing thermal decomposition.

The particular collection and detection system 600 to be used may be based on factors such as a desired period between maintenance sessions, ease of maintenance, or cost. FIGS. 6A-6B illustrate an implementation involving a carousel wheel 610 with a reusable discreet collection material 520. Other implementations, such as a "reel-to-reel" system with a one time or reusable collection material 520, also may be used. Such a reel-to-reel mechanism may be more costly to build and more difficult to maintain (e.g., by replacing the worn collection material 520) than the carousel wheel 610. Because the reel-to-reel mechanism could hold more collection material, the time between replacements may be greater than for the carousel implementation.

In the illustrated implementation including a carousel wheel 610, the collection material 520 is within the carousel wheel 610 and includes either a series of discreet collecting areas or a continuous collecting area. In a series of steps, the collection and detection system 600 gathers collected material onto an area of the collection material 520 and then rotates to the decomposition and analysis system 630 to enable the deposited material to be analyzed to detect the presence of particles of materials.

According to various implementations employing the carousel wheel, a first station is the impact collector 500, which may seal to the carousel wheel 610. The term "station" refers to specific locations or degrees of rotation of the carousel wheel 610. The position of stations may be determined by the position of holes along the circumference at angular positions of the carousel wheel 610. After particles are deposited with the impact collector 500 to an area of the collection material 520, the carousel wheel 610 rotates to the second station, which is the decomposition and analysis system 630. Characteristics of the decomposition and analysis system 630 depend on the detection unit employed.

A media moving mechanism 660 is employed to rotate the collection material 520, and in the implementation discussed above, the carousel wheel 610. For a high degree of positional accuracy, a stepper motor may be employed. As a stepper motor is expensive and requires specialized electronics to control, a simpler alternative that may be used is a unidirectional or bidirectional DC motor. An LED optical sensor may be used to determine and control the position of the media moving mechanism 660. Maintenance of the carousel wheel 610 may be conducted through an automatic disc loading and unloading station to extend the time between routine replacement of the collection material 520 to, for example, one month.

In one implementation that includes resistive heating, the collection material 520 area is three $cm^2$ and includes two contacts which are placed at opposite ends of the collection material 520. The contacts may be shaped in various ways, such as, for example, raised metallic bumps (e.g., like a contact for a battery), rods, or plates. A spring loaded contact may be used to complete the connection. The carousel wheel 610 may be designed with upper and lower halves. In one assembly method, the two halves are separated, the collection material 520 is installed on the bottom half, and the top half is attached on top of the collection material 520 forming a sandwich. In one implementation, for each portion of the collection material 520, one of the contacts is in the form of an electrode which is tied to a single common connection point (not shown), and the other contact 660 is a unique connection. In such an implementation, the common connection point is constantly connected to the power supply, and only one unique connection is connected at a time to enable only one portion to be resistively heated. The collection material 520 may include holes for the optical sensors (or LED sensor as discussed above with respect to the carousel wheel 610 implementation).

Residual material, such as oils, may contaminate or mask later measurements, or may shorten the life of a reusable collection material 520. By heating the collection material 520 to a higher temperature than that required to trigger decomposition of energetic material, such residual material may be burned off. Optionally, a high temperature bake out at temperatures in excess of 300° C. may be conducted in order to thermally decompose remaining particles.

A pyrometer may be included in the decomposition and analysis system 630 or the heating controller 650. During heating, there is slight expansion of the collection material 520. In order to prevent distortion, the design is such that there is a slight tension on the collection material 520.

Figure 6C:
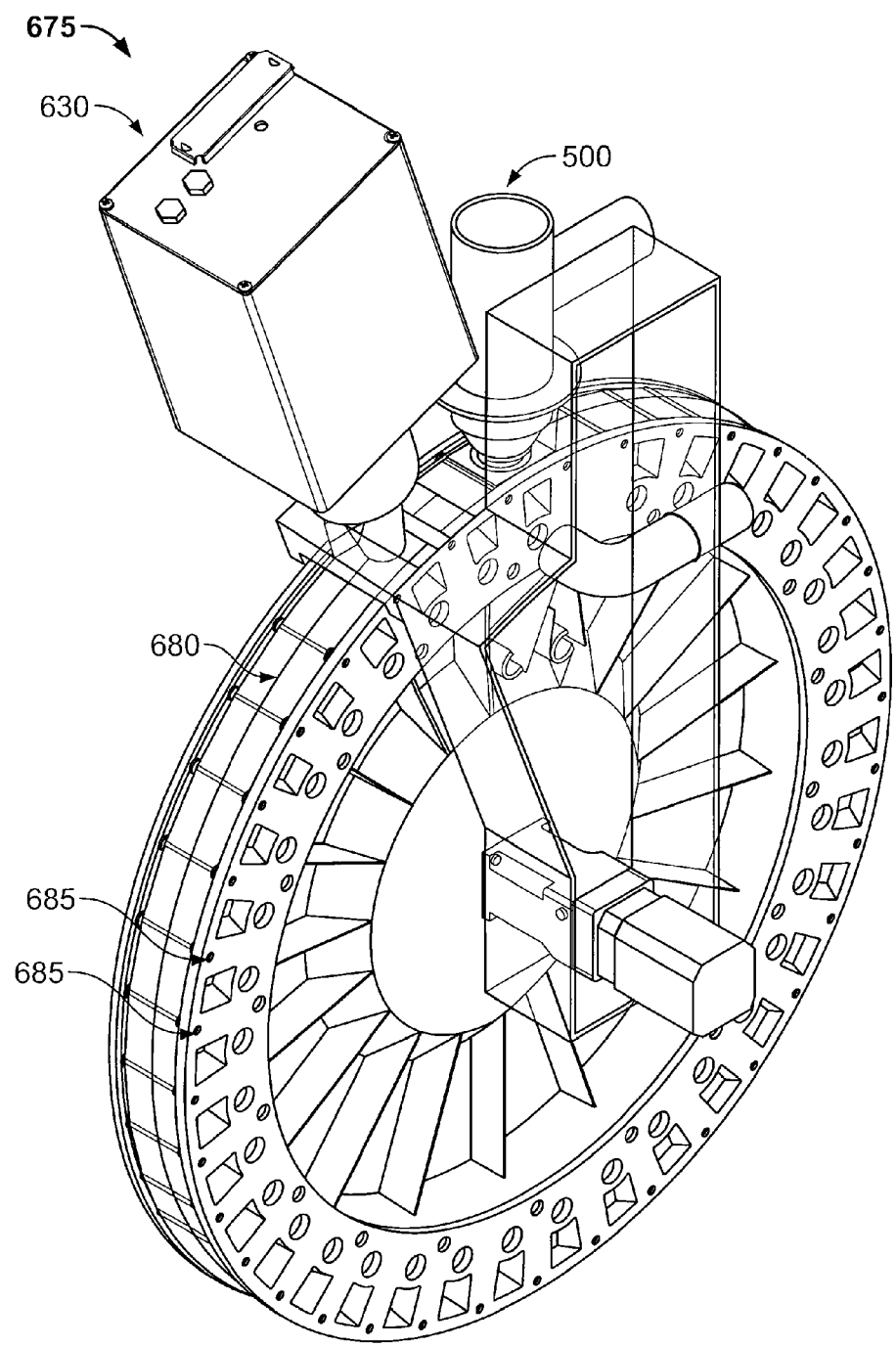
FIG. 6C illustrates a collection and detection system with a continuous collection material.

Referring to FIG. 6C, a continuous collection material system 675 includes a continuous conductive collection material 680, and discrete contact points 685. In the system 675, the continuous material 680 is wrapped around the width of a wheel. A portion of the continuous material 680 is within the impact collector 500 where particles may be deposited. As the wheel rotates, the portion moves within the decomposition and analysis system 630.

The continuous system 675 includes numerous discrete contact points 685 where an electrical connection is established. When the decomposition and analysis system 630 is activated, discrete contact points 685 are used to generate a current through the continuous material 680, resistively heating the particles. In order to prevent an electrical path through the full circumference of the continuous material 680, a portion of the continuous material 680 may be left black or otherwise severed.

The previous description provides exemplary implementations of a collection and detection system 600. Other implementations may include different features, such as a checking solution injected onto the collection material 520 on an infrequent but scheduled basis to test the ability of the system to successfully detect particles of a material. This mechanism may include a reservoir that needs to be replaced periodically and may include, for example, a LEE miniature variable volume pump model number LPVX0502600B, available from the Lee Company of Westbrook, Conn. (see www.theleeco.com) or a small KNF model UNMP830 available from KNF Neuberger, Inc. of Trenton, N.J. (see www.knf.com) or similar pump and a LEE solenoid valve similar to LEE model number INKX051440AA.

Figure 7A:
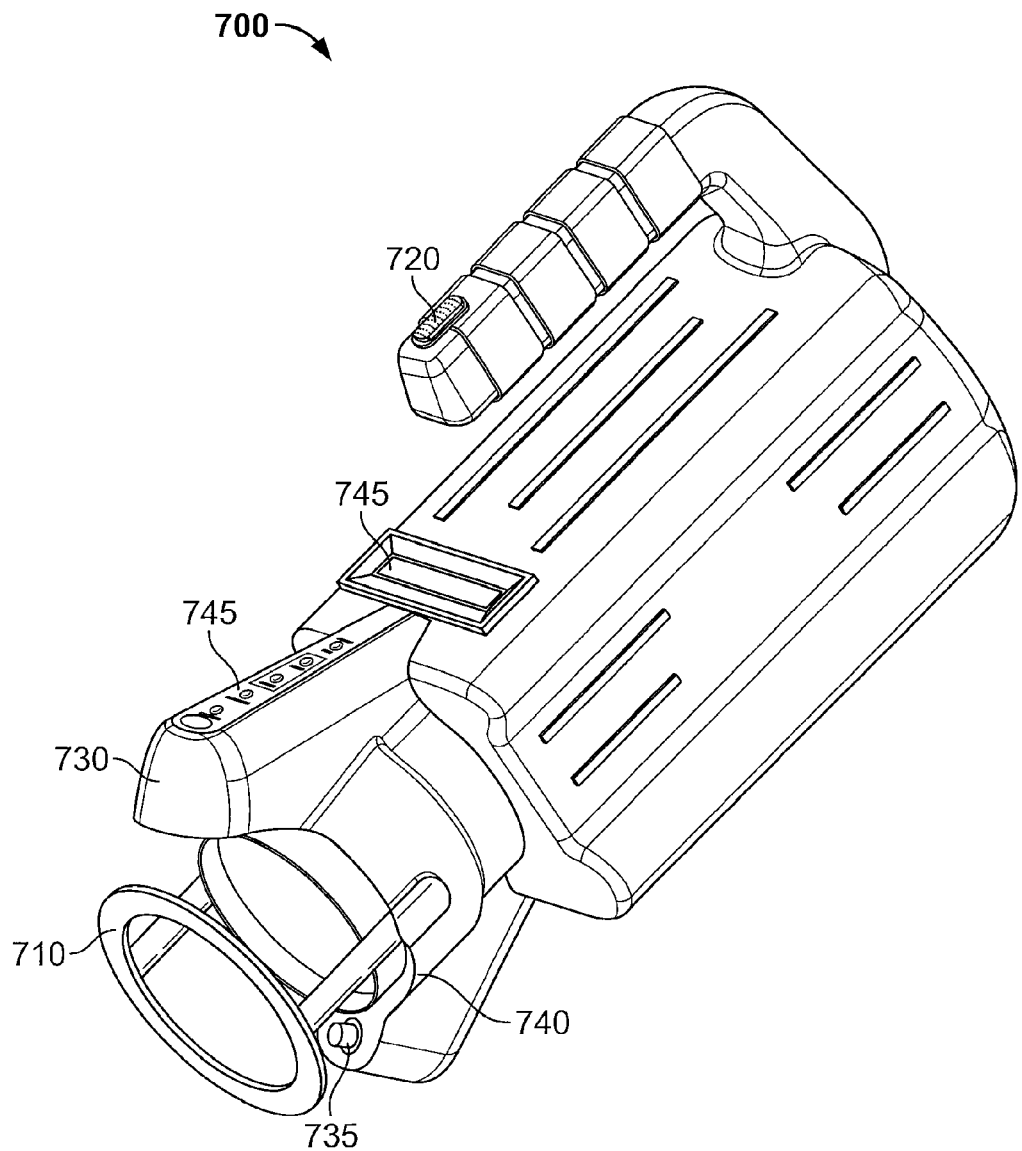
FIG. 7A illustrates a hand-held detection system.

Referring to FIG. 7A, a hand-held detection device 700 includes a standoff ring 710, a trigger 720, a flash-lamp 730, a pyrometer 735, an IR-detector array 740, and output displays 745. The device 700 may be brought to the sample in order to detect explosive particles.

In order to operate the device 700, the user first places the standoff ring 710 on the area to be scanned for explosive particles. The standoff ring 710 provides an appropriate distance between the sample and the IR detector array 740. Next, the user operates a trigger 720 to activate the flash-lamp 730 and cause heating. The flash-lamp 730 is aimed at the standoff ring 710 and heats the sample to trigger thermal decomposition. The real-time temperature of the sample is measured through the pyrometer 735, and such measurement is a part of a feedback loop to enable the temperature to be actively controlled by the flash-lamp 730. The IR-detector array 740 detects decomposition by explosive materials. The detected results are indicated by the output displays 745.

Figure 7B:
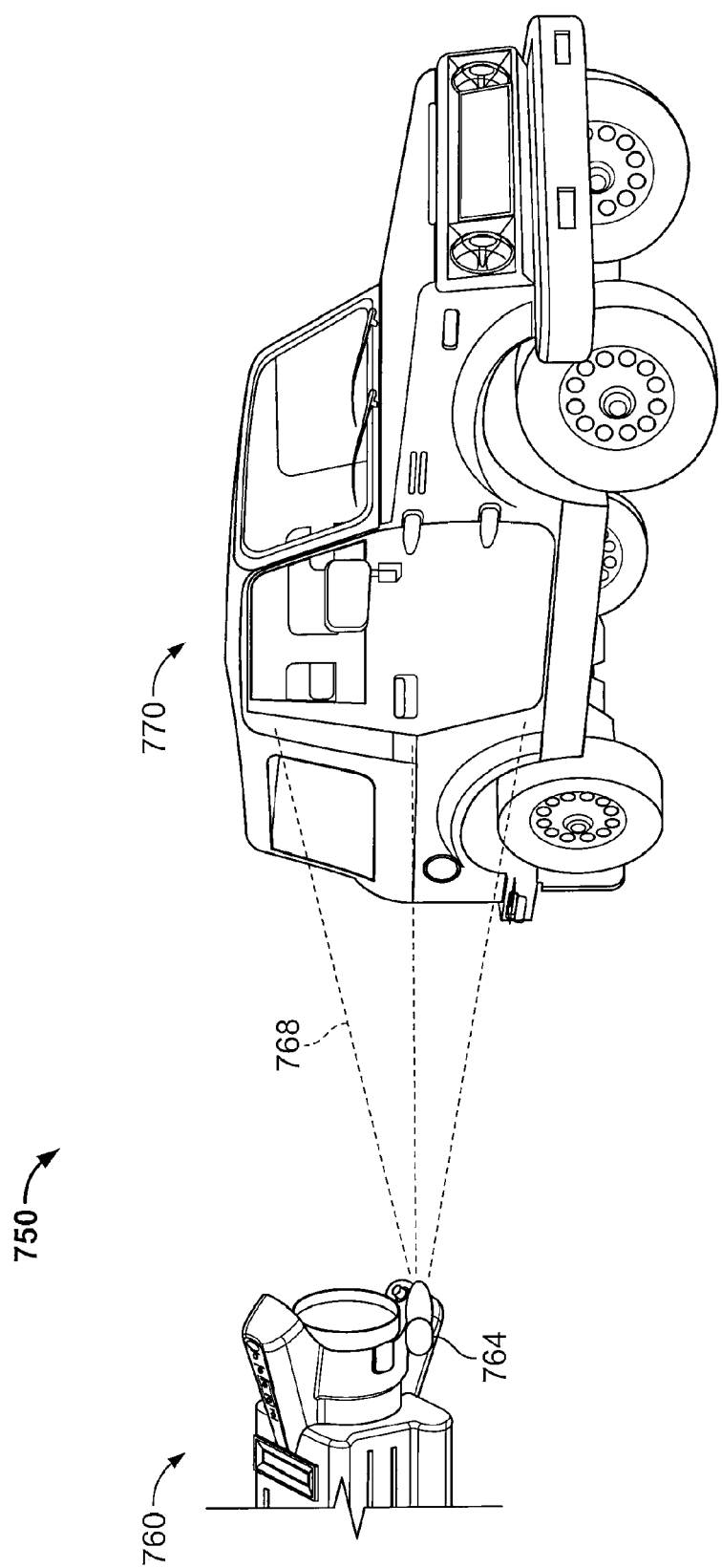
FIG. 7B illustrates a ranged detection system.

Referring to FIG. 7B, a long-range detection system 750 includes a detection device 760 that operates as described above and may be aimed at an object 770 at a distance. In the system 750, the detection device 760 emits radiation in the direction of the object 770. After striking the object 770, the radiation causes localized heating that triggers thermal decomposition of trace explosive particles. IR radiation released from the decomposition is detected by the detection device 760.

In particular, the detection device 760 includes a flash-lamp 764 and a distance focused IR detector array 768. The flash-lamp 764 emits a pulse of high-energy radiation sufficient to cause thermal decomposition at the object 770. Emitted IR radiation strikes the IR detector 768 which enables a positive identification of trace explosives.

The detection device 760 may be enabled to operate at a distance of tens to hundreds of meters from the object 770. Laser heating may be used as an alternative to flash-lamp heating. Laser hardware may be considerably more complex, power consuming, and expensive than hardware required for resistive or flash-lamp heating. As such, the use of a laser may be practical in implementations where the object 770 is at a considerable distance beyond the immediate vicinity of the detection device 760. Also, a telephoto lens may be included that focuses the IR detector array 768 on an appropriately small area. In one implementation, the telephoto lens focuses the IR detector array 768 such that the array views the object 770 at a resolution that is similar to the resolution of FIG. 1.

In one implementation, a checkpoint for explosives equips a detection device 760 to detect vehicles for explosives. The detection includes operation of the flash-lamp across the sides of vehicles to detect explosives along various areas of the object 770 being scanned.

The previous descriptions provide exemplary implementations of handheld and range detection devices. Other implementations may include other, or different features. For example, various implementation, the detection device may be mounted in a variety of vehicles, such as, for example, an armored personal carrier, a tank, an aircraft, or a seacraft.

Figure 8A:
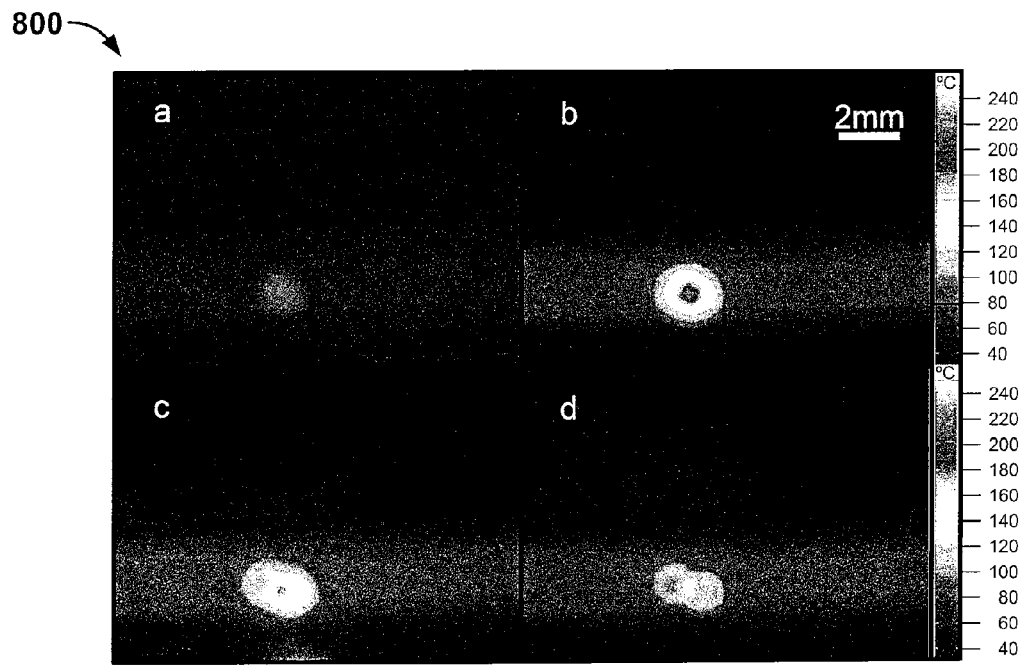
FIGS. 8A and 8B illustrate particle detection data.

FIG. 8A shows data 800 of an exothermic decomposition detection. In particular, a picture is shown of a sample media with a decomposing material at four different instances of time. Specifically, data 800 for the energetic detection of a particle of smokeless powder using a 60 Hz frame rate are shown. Element (a) shows an initial IR image with a relatively cool particle and filament. Next, element (b) shows an IR image showing elevated temperatures around the particle just prior to explosion. Next, element (c) shows an IR image showing the particle explosion. Finally, element (d) shows an IR image showing elevated gas temperatures resulting from the particle explosion.

Figure 8B:
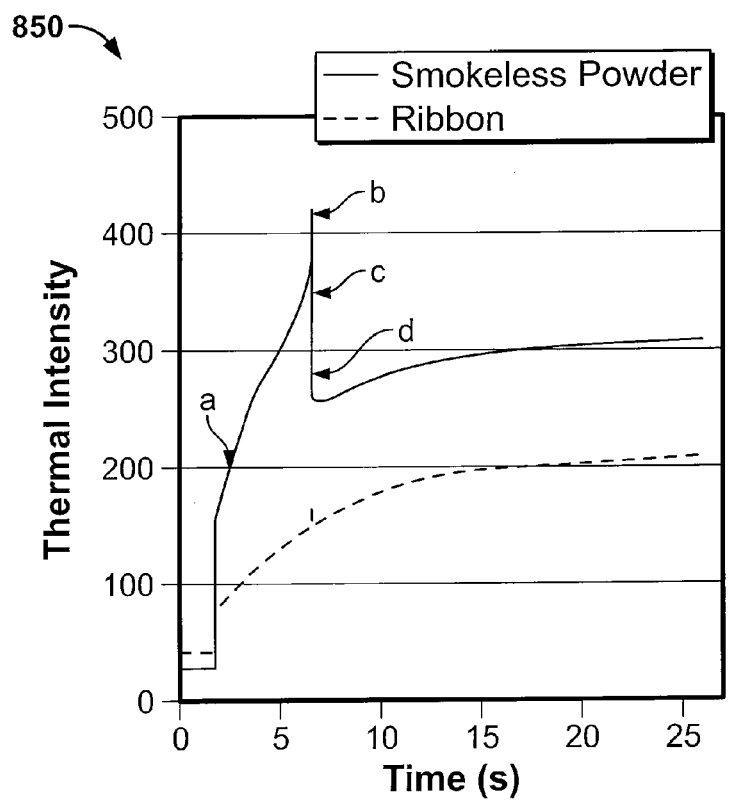

Referring to FIG. 8B, data 850 for the same decomposition are shown from the perspective of a pixel viewing the smokeless powder and a pixel viewing the sample media across time. In the data 850, the four instances of time from the data 800 of FIG. 8A are marked. Specifically, two-dimensional plots of the thermal signatures of one pixel viewing the smokeless powder and one pixel viewing the sample media are shown.

Analytical interpretation of the results is possible by examining the temperature of individual pixels or the average of several pixels as a function of time. Results may demonstrate that a particle's rapid increase in temperature exceeds that of the collection material. This feature can be used in processes to automatically detect the presence of explosives. In particular, each energetic compound has a quantifiable and positive heat of decomposition (H) and a quantifiable activation energy (E). H impacts the total heat that is released and E the rate of heat release. These two properties interact in such a way that a detector may distinguish classes of explosives and/or the chemical composition.

Automatic process based target recognition is used to track multiple pixels simultaneously and to automatically recognize the unique characteristics of explosives. Simple enhancements include subtraction of the varying background temperature, and displaying the differential so as to better visualize the peak maximum. Local maxima and/or minima in a temperature versus time plot are indicative of the presence of explosives and are mathematically defined as points at which the time rate of change of the temperature equals zero (i.e., $dT/dt=0$). However, local maxima due to the fluctuating temperature of the collection material may also be present. To correct for these artifacts, the collection material temperature may be subtracted from the temperature recorded at various points.

Figure 9A:
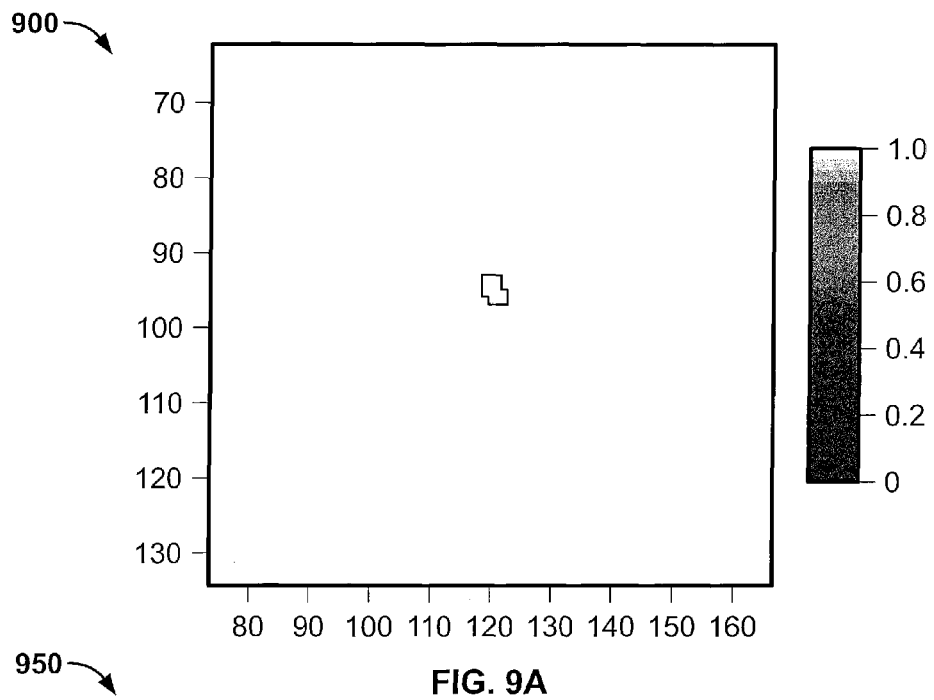
FIGS. 9A and 9B illustrate processed particle detection data.

FIG. 9A shows processed data results 900 of a detected exothermic decomposition. To determine the results 900, a process is used to analyze the time derivative of the raw data for a threshold level that is characteristic of an explosive. The raw data was obtained by heating 100 nanograms of triacetone triperoxide (TATP) to trigger exothermic decomposition. As seen from the image, approximately 12 pixels exceeded a threshold analytically determined by the process. This level of response for TATP correlates to a detection limit of 8 nanograms/pixel.

Figure 9B:
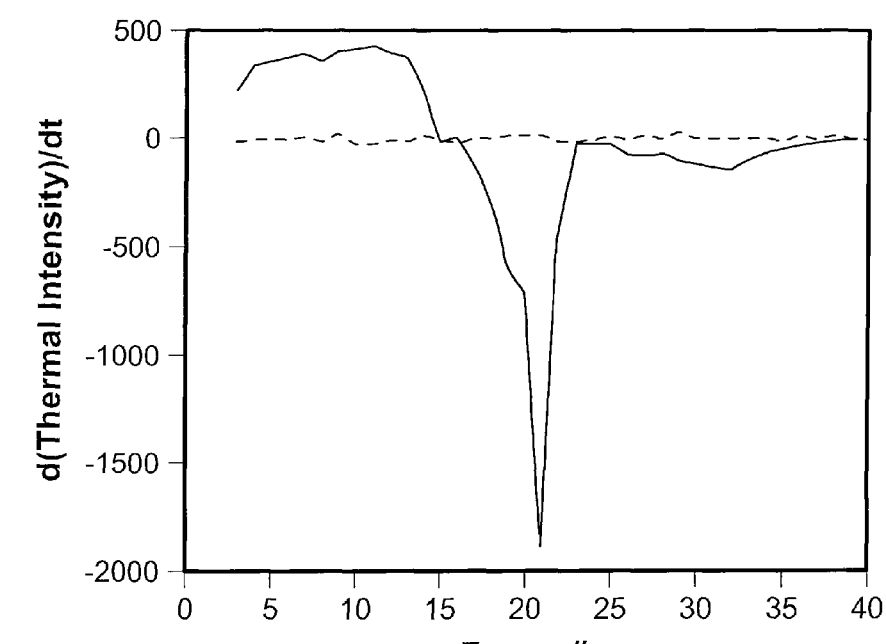

Referring to FIG. 9B, the plot 950 shows a pixel at (95, 123) with a background pixel at (110, 140), from the processed data results 900 of FIG. 9A. Detection of RDX, TNT, TATP and ANFO have all been verified at the 100, 25 and even sub 10 ng level on dirty substrates under conditions typical of use. Detection has also been demonstrated for explosive materials such as PETN, Benzoyl Peroxide, ammonium perchlorate and smokeless powder.

Testing was also performed for potential interference materials such as sugar, diesel fuel, gasoline, numerous hand creams and lotions, perfumes, dandruff, human skin oils, wipings of sweat from the back of the neck, and fingerprints from touching salami, bacon and other preserved meat and fish products, all of which gave a clear "no-alarm" signal.

Figure 10:
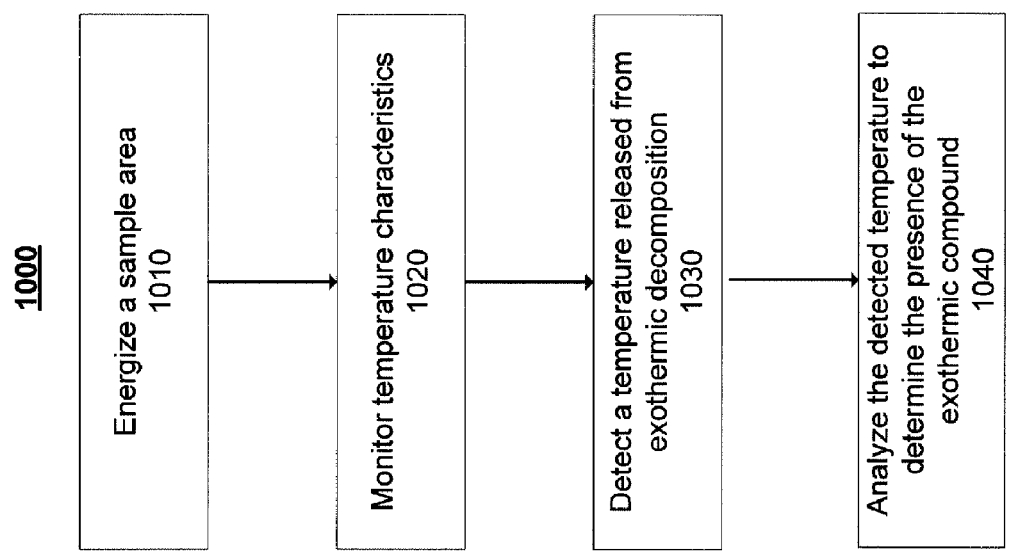
FIGS. 10 and 11 are flow charts of methods of detecting energetic materials.

Referring to FIG. 10, detecting energetic materials, such as explosives, includes energizing a sample area, monitoring temperature characteristics, detecting a temperature released from exothermic decomposition, and analyzing the detected temperature to determine the presence of the exothermic compound.

A sample area is energized (step 1010). As shown with respect to FIGS. 2 and 3, energizing the sample area may include resistive or radiative heating. When the sample area is at a large distance from the energizing mechanism, other methods, such as lasers may be used.

Radiant energy or temperature characteristics of the sample area are monitored (step 1020). Energy corresponding to the sample area's temperature may be detected by using a sensor focused on the sample area. An infrared sensor may be used to sense infrared emissions from the sample area as well as a surrounding material or collection area.

Heat either measured either as radiant energy released or temperature change from exothermic decomposition is detected (step 1030). Specifically, as an exothermic compound in the sample area heats, the exothermic compound may undergo thermal decomposition. Energy released from the thermal decomposition may be detected by the sensors monitoring the radiant energy or temperature characteristics.

The detected radiant energy or temperature is analyzed to determine the presence of the exothermic compound (step 1040). The analysis may include determining an energy or temperature difference between an area and its surroundings, or a time rate of change of energy or temperature. The analysis also may include determining a heat of decomposition or an activation energy of the thermal decomposition. Determined information may be used to determine a specific type or category of explosive that underwent exothermic decomposition.

Various implementations employ several other benefits. For example, the performance of the detector may not be adversely affected by the presence of a massive overload of background materials. In particular, there may not be degradation in performance when the sample is coated in oily substances and even when smoke is clearly visible. With the detector, there may be immediate recovery from massive overloads as big as 2,000 ng of material. Further, the detector may detect chemicals that conventional detectors may miss, such as, ammonium nitrate, nitro cellulose, TATP, benzoyl peroxide, ammonium perchlorate, other explosive chemicals, or mixtures of unknown chemistry. In general, if a material can explode, the material's presence may be detected through thermal decomposition.

Figure 11:
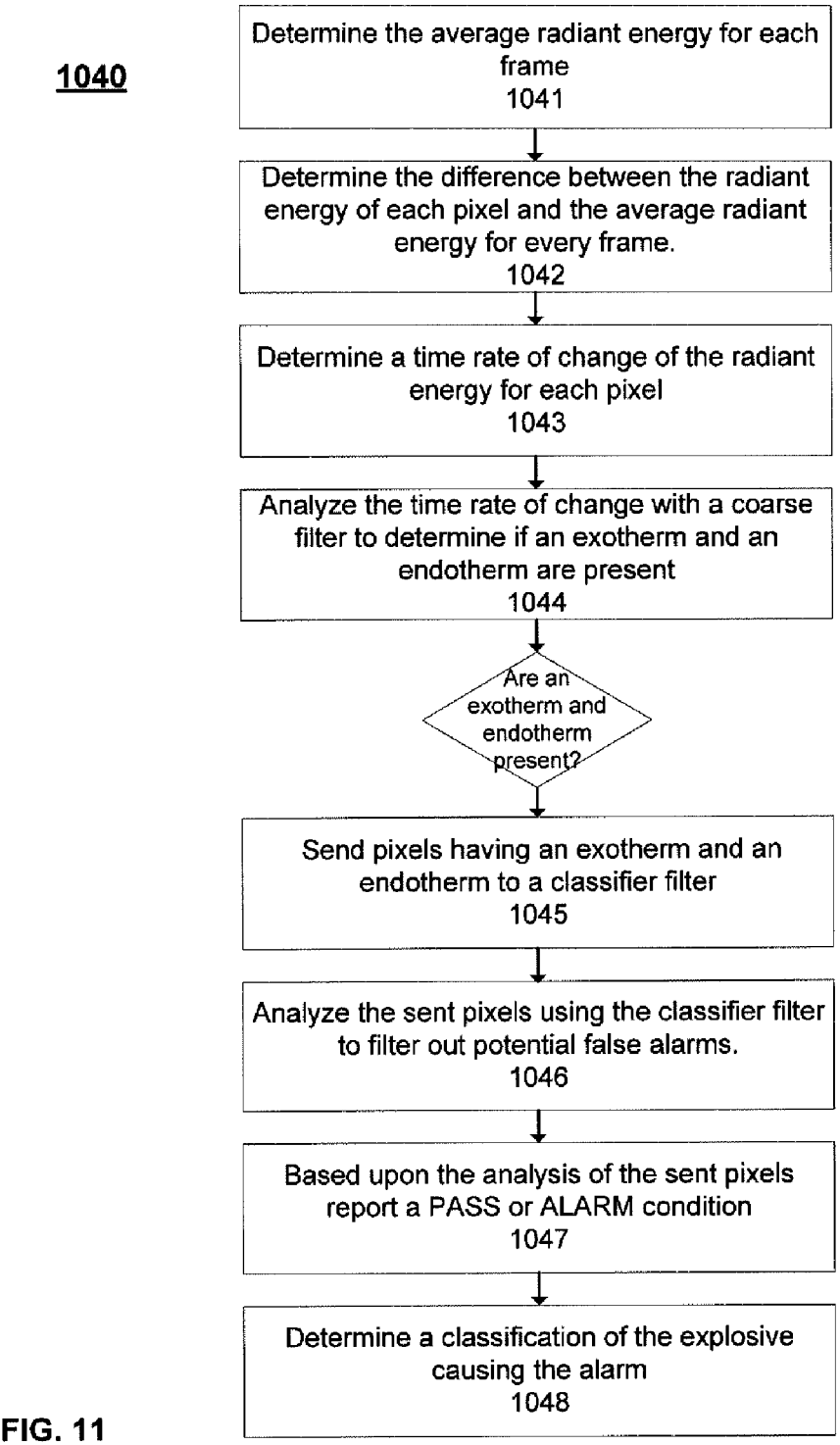

In greater detail, and referring to FIG. 11, an example process 1040 analyzes a time-dependent thermal signature to determine the presence of an exothermic compound (such as an explosive). In general, the process 1040 may be used to detect trace amounts of common military explosives, such as RDX, TNT, and PETN; commercial explosives such as ammonium nitrate, nitrocellulose, and smokeless powder; and homemade explosives such as hydrogen peroxide, peroxide and sugar mixtures, TATP, benzoyl peroxide, and ammonium perchlorate.

In particular, the process 1040 determines whether an exothermic compound, such as an explosive, is present based on analysis of a time-dependent thermal signature of each pixel included in a detector array used to monitor a thermal energy status of a sample area as the sample area is heated. The thermal energy status of the sample area may be the radiant energy released from or absorbed by the sample area and/or it may be the temperature of the sample area. In general, the heat released from the sample area as it is heated may be detected by the detector as radiant energy. The detected radiant energy may be used to determine a time-dependent thermal signature of the sample area. In other implementations, the detected radiant energy may be converted to a corresponding temperature. In this implementation, the time-dependent thermal signature is based on the temperature of the sample area as the sample area is heated over time.

As discussed in more detail below, analysis of the time-dependent thermal signature for characteristics of an explosion may allow a determination of whether the sample area includes explosive materials. For example, supplying an explosive material with sufficient energy (e.g., the activation energy) causes the explosive to explode. When the explosion occurs, heat is released from the explosion into the surrounding environment. This heat release may be referred to as an exotherm, and the exotherm is typically characterized by a rapid increase in the radiant energy released from the sample area. The explosive material is consumed during the explosion. After the explosive material is consumed, the explosion ends, and the sample area cools to the surrounding temperature. This cooling may be referred to as an endotherm. The endotherm is typically characterized as a decrease in the radiant energy released from the sample area.

Thus, time-dependent thermal signatures of explosives include an exotherm (a rapid rise in radiant energy over a first time interval) followed by an exotherm (a decrease in radiant energy over a second time interval). Because time-dependent thermal signatures of materials other than explosives generally do not include an exotherm followed by an endotherm, the presence of an exotherm followed by an endotherm in a time-dependent thermal signature indicates that the thermal signature was created by heating an explosive material. Additionally, because thermal signatures of explosives tend to have an exotherm followed by an endotherm, this type of analysis allows almost any type of explosive to be detected without the use of additional a priori information about the thermal signature of the explosive. For example, analyzing thermal signatures for the presence of an exotherm and an endotherm allows a determination of whether explosives are present without comparing the thermal signature to signatures included in a predefined library of thermal signatures.

Figure 12A:
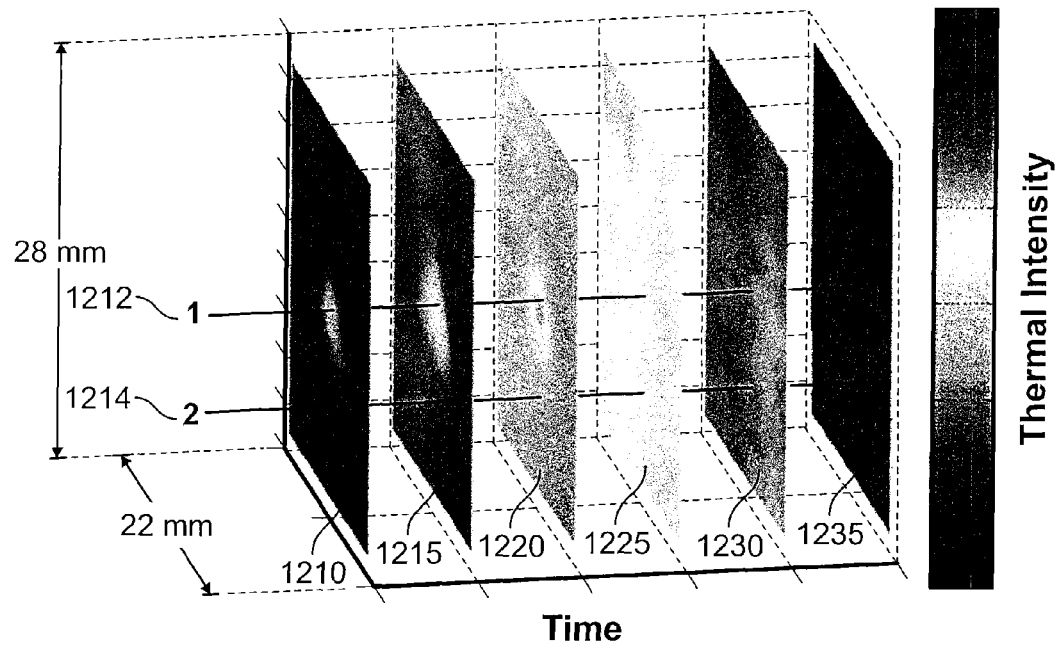
FIGS. 12A and 12B are illustrations of data used by a method of detecting energetic materials.
Figure 12B:
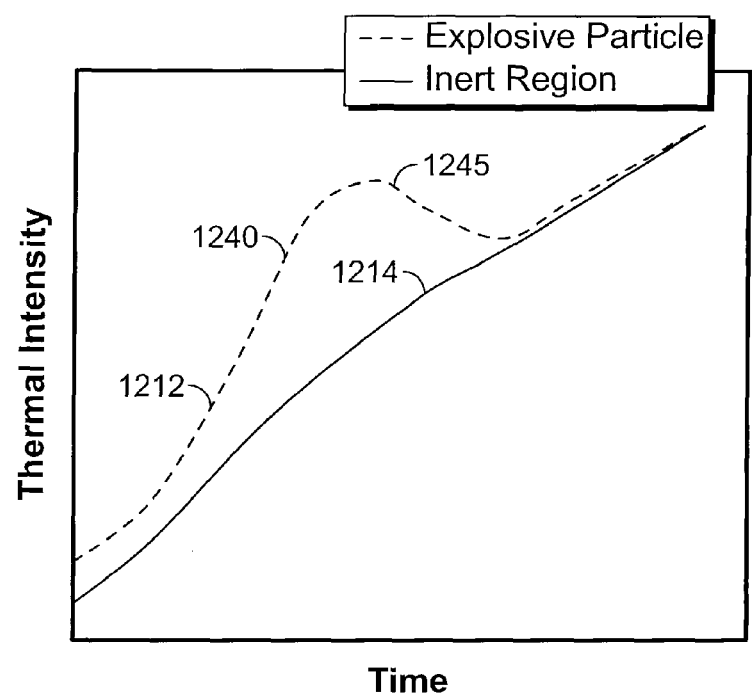

The process 1040 may analyze the radiant energy released over time from the sample area to determine if the sample area includes explosive material. As discussed above, the radiant energy of a sample area is monitored using, for example, an infrared camera. An example of data collected from the monitoring, which may be used in the process 1040, is shown in FIG. 12. In the example shown in FIG. 12, data is collected using, for example, an infrared sensor by taking snapshots, or frames, (such as snapshots 1210, 1215, 1220, 1225, 1230, and 1235) of the sample area at various times.

Each pixel in each frame represents the radiant energy measured at each pixel included in the infrared sensor. In some implementations, each pixel in the frame may be converted to a temperature based on a predefined temperature conversion. However, using the directly measured radiant energy, as opposed to the radiant energy converted into a temperature, may allow for more efficient and simpler processing due to the elimination of the conversion process. Using the directly measured radiant energy also may produce more accurate results by eliminating errors that may occur during the conversion from radiant energy to temperature. Moreover, using the directly measured radiant energy may provide more control over the processing of data because the conversion from radiant energy to temperature is generally preformed by predefined conversions included in the detector software.

In the example shown in FIG. 12, the infrared sensor that includes an array of 320×240 pixels monitors a sample area that is 28 millimeters tall and 22 millimeters wide. The frames may be collected at regular intervals. For example, the frames may be collected at a rate of 60 frames per minute such that one frame is collected every 16.7 milliseconds. The example shown in FIG. 12 includes six frames, however more or fewer frames may be collected. For example, the frames may be collected for two seconds.

The process 1040 analyzes the frames to determine a time-dependent thermal signature of each pixel, and the thermal signature is used to determine whether explosives are present in the region of the sample area imaged by that pixel. The frames 1210, 1215, 1220, 1225, 1230, and 1235 image the sample area and include a target region 1212 and an inert region 1214. In the illustration shown in FIG. 12, the target region 1212 includes explosive materials and the inert region 1214 does not. The inert region 1214 also may be referred to as the background or the surrounding region. As seen in FIG. 12, as heat is applied to the sample area, the amount of heat released from the target region 1212 is different from that released from the inert region 1214.

Referring again to FIG. 11, the average radiant energy is determined for each frame (step 1041). For example, the value of each pixel in each of the frames 1210, 1215, 1220, 1225, 1230, and 1235 may represent the radiant energy released by the region of the sample area imaged by the pixel. Thus, the average value of the pixels in the frame 1210 represents the average radiant energy released by the sample area at the time when frame 1210 was collected. In another example, each pixel in each of the frames 1215, 1220, 1225, 1230, and 1235 may be converted from radiant energy to temperature. In this example, the average of the values of the pixels in the frame represents the average temperature of the sample area.

The difference between the radiant energy at each pixel and the average value is determined for each pixel in each frame (step 1042). Thus, the average value for a particular frame determined in (step 1041) is subtracted from the value of each pixel in that frame. Accordingly, the thermal energy status (e.g., the radiant energy or temperature) as a function of time may be determined for each pixel. For example, and referring to FIG. 12B, the value of the radiant energy of the pixel 1212 and the pixel 1214 as a function of time are shown. The pixel 1214 images a portion of the sample area that does not include explosive material, and the pixel 1212 images a portion of the sample are that includes explosive material. As compared to the pixel 1214, the radiant energy of the pixel 1212 increases at time 1240 (an exotherm) as the explosives the pixel images are heated and explode and the radiant energy of the pixel 1212 decreases at time 1245 as the explosion consumes the explosive material and the area that the pixel 1212 is imaging cools (an endotherm).

Figure 13A:
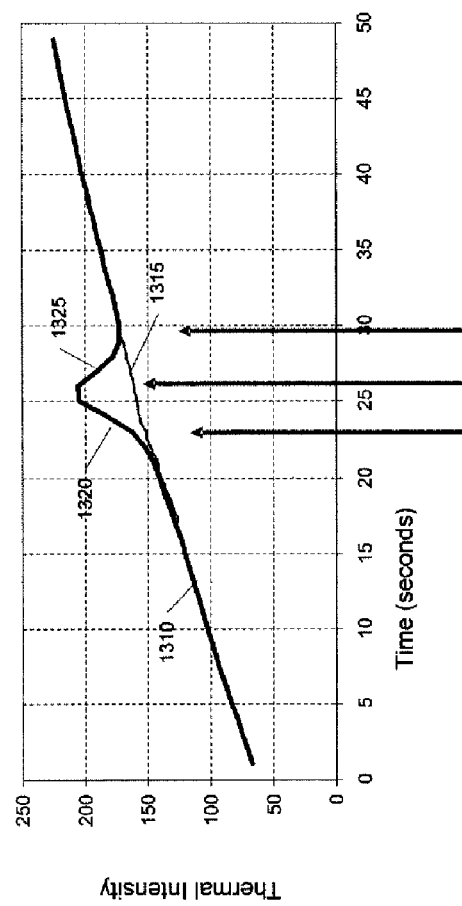
FIGS. 13A, 13B, 14A-14C, and 15A-15C are illustrations of time-dependent thermal signatures of energetic materials.
Figure 13B:
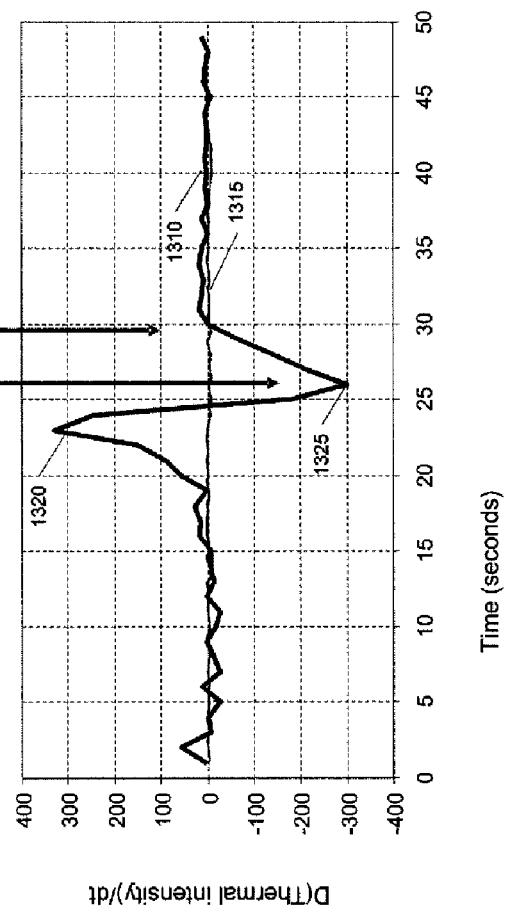

A time rate of change (e.g., a derivative with respect to time) is determined for each pixel (step 1043). The time rate of change may be the time rate of change of the radiant energy or the temperature. An illustration of the radiant energy and the time rate of change of the radiant energy detected by a pixel that images explosive material, such as the pixel 1212, and a pixel that images a region without explosive material, such as the pixel 1214, are to shown in FIGS. 13A and 13B, respectively. In particular, FIG. 13A is an illustration of thermal intensity versus time for a pixel 1310 that images a region that includes explosive material and a pixel 1315 that images a region without explosive material. FIG. 13B is an illustration of a derivative with respect to time for the radiant energy detected by the pixels 1310 and 1315. The time rate of change of the pixel 1310 may be determined by comparing the value of the pixel 1310 in one with the value of the same pixel in a previously or subsequently collected frame. The time rate of change may be determined in any manner that a derivative may be determined. For example, the comparison may be a subtraction, and the resulting value is generally divided by the time that elapsed between collection of the frames. In general, the comparison is performed between the same pixel in two different frames after the average value for each frame is subtracted. However, in some implementations, the comparison may be done without subtracting the average value from the frames.

Accordingly, the time rate of change for each pixel is determined. The time rate of change may be the time rate of change of the radiant energy detected by that pixel or the time rate of change of the temperature of the region of the sample area the pixel is imaging. The time rate of change for each pixel may be the time-dependent thermal signature of the region of the sample area that is imaged by the pixel. In other implementations, the time-dependent thermal signature may be the radiant energy of the pixels over time. In still other implementations, the time-dependent thermal signature may be the temperature of each pixel over time. Referring to FIG. 13B, the time rate of change of the pixel 1310 includes an exotherm 1320 and an endotherm 1325. The endotherm 1320 and exotherm 1325 are also apparent in the data shown in FIG. 13A. The presence of the exotherm 1320 and the endotherm 1325 indicates that an explosive is present.

Referring again to FIG. 11, the time rate of change (e.g., time-dependent thermal signature) determined for each pixel in (step 1043) is analyzed by a coarse filter to determine whether an exotherm and an endotherm are present in the time-dependent thermal signature (step 1044). The coarse filter is applied to the time-dependent thermal signature of every pixel. The coarse filter is designed to have a high probability of detection, but not necessarily a low false alarm rate. In some implementations, the coarse filter may have both a high probability of detection and a low false alarm rate.

Pixels having a time-dependent thermal signature without an exotherm and an endotherm generally are not of further interest because, as described above, these pixels are almost certainly not imaging explosive materials. In contrast, pixels that have a time-dependent thermal signature that includes an exotherm and an endotherm are most likely imaging explosive materials. The time-dependent thermal signatures of these pixels are sent to a classifier filter (step 1045). The classifier filter is a more refined filter that analyzes the time-dependent signatures of the pixels that have an exotherm and an endotherm in more detail than the coarse filter. In particular, the classifier filter reduces the false alarm rate.

An indication of whether the sample area includes explosive materials is produced (step 1047). For example, the process 1040 may report a PASS (e.g., no explosive materials present) or an ALARM (e.g., explosive materials present) indication. In general, if any of the time-dependent thermal signatures analyzed in (step 1045) indicate that explosive material is present, an ALARM indication is produced. In some implementations, the coarse filter is not applied, and the PASS or ALARM indicator is produced based on whether the classifier filter determines if any of the time-dependent thermal signatures includes an exotherm and an endotherm. Other indicators also may be produced. For example, in some implementations, an ERROR indicator may be produced. For example, the ERROR indication may be a result of a system malfunction, such as a malfunctioning detector. In another example the ERROR indication may result from not being able to heat the sample area due to environmental conditions.

Figure 14A:
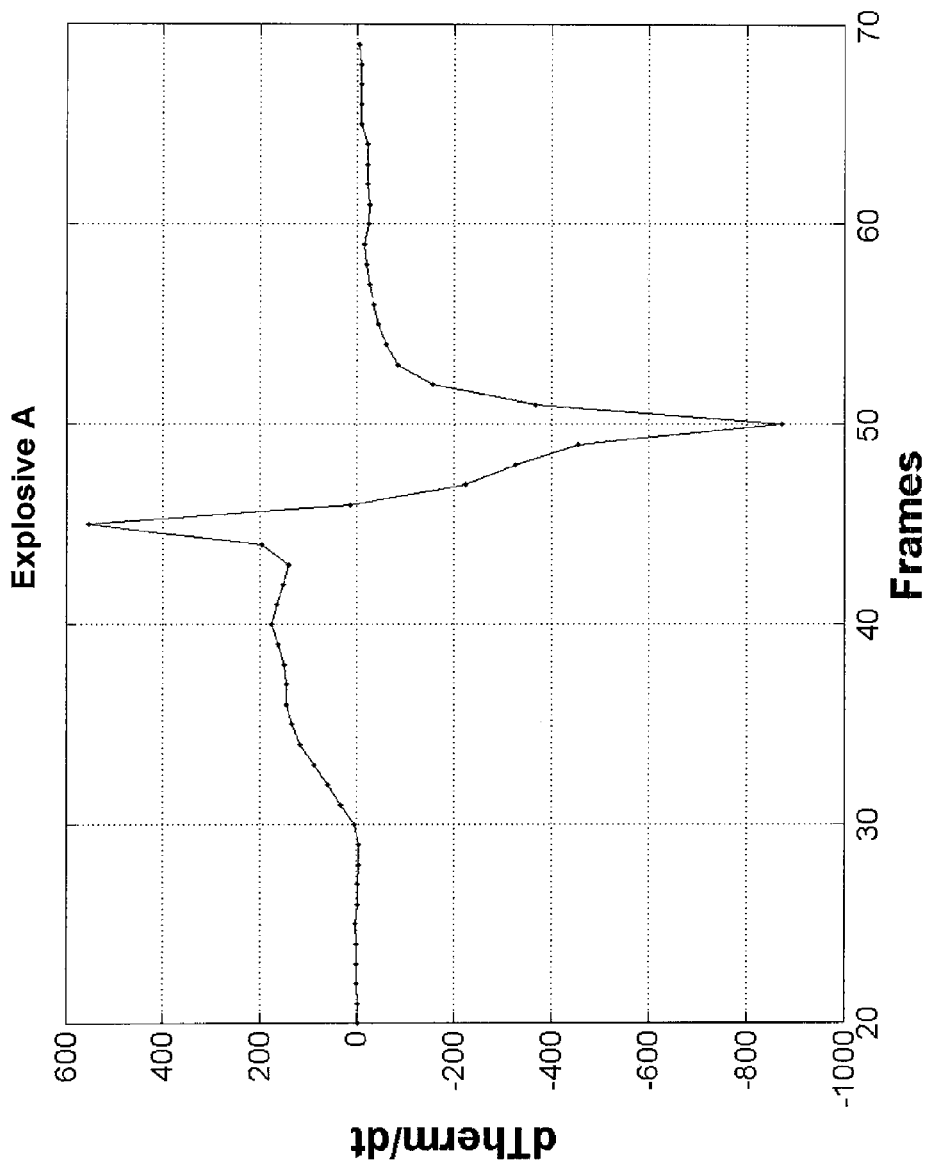
Figure 14B:
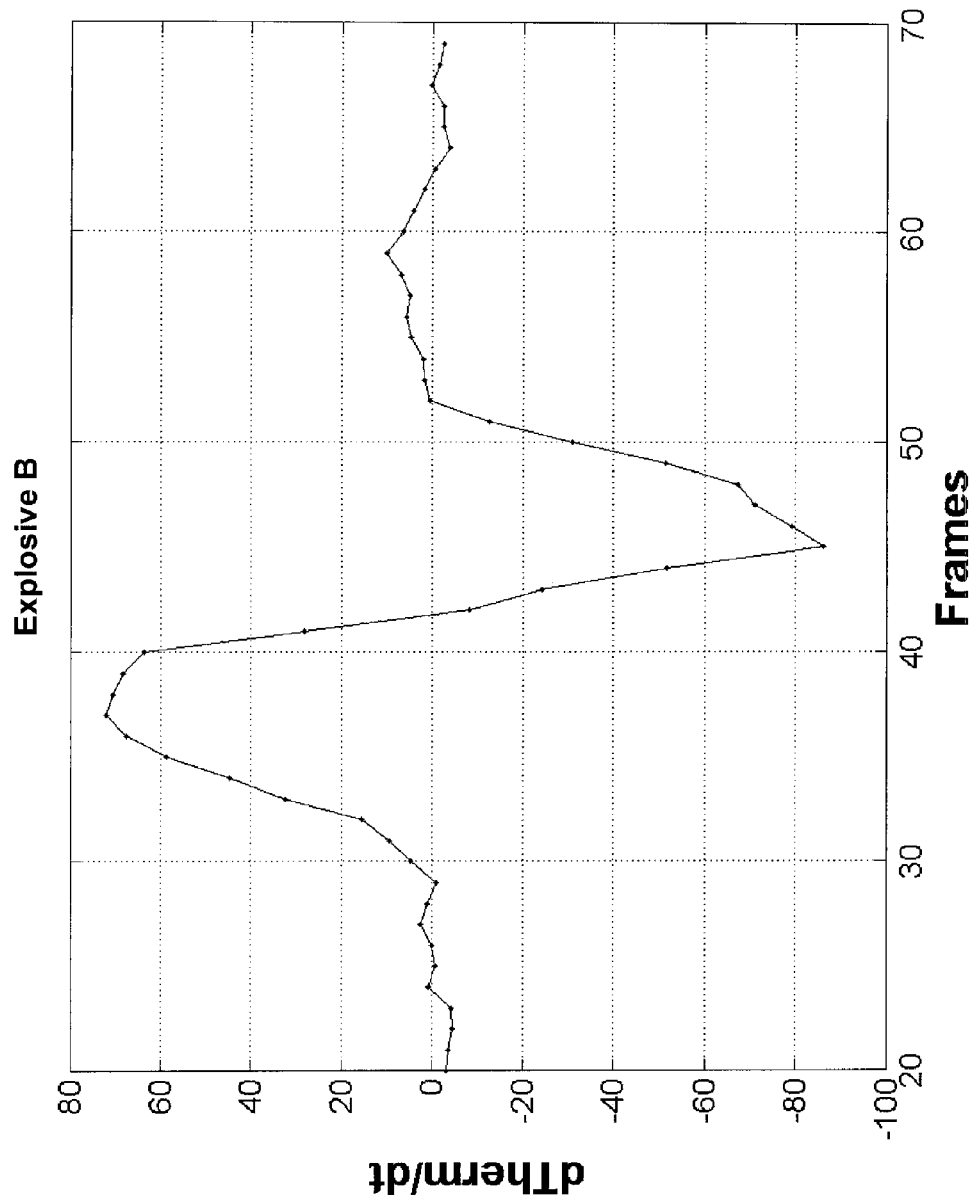
Figure 14C:
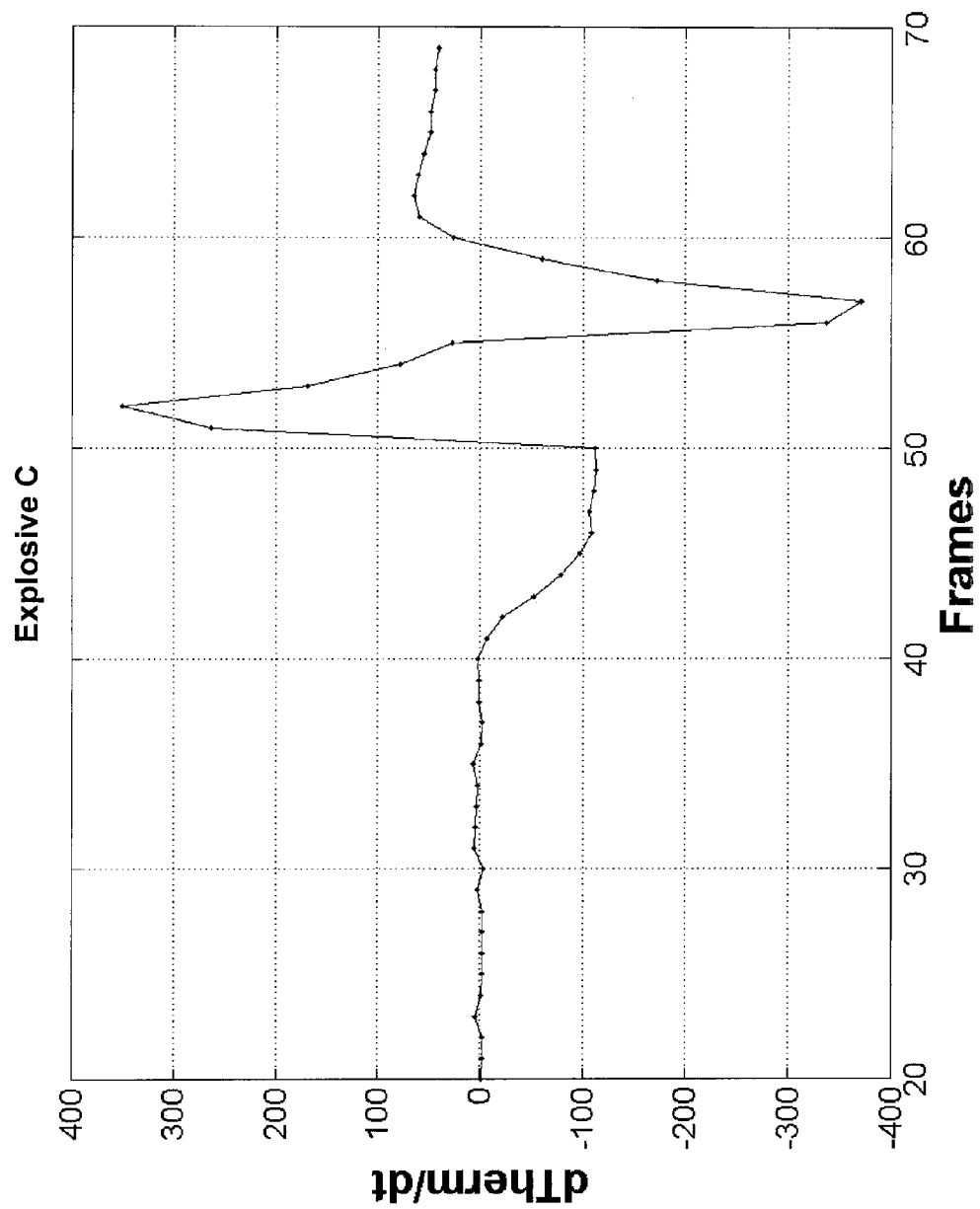

Pixels having time-dependent thermal signatures that include an exotherm and an endotherm are analyzed further to determine a classification of the explosive material that caused the ALARM indication (step 1048). Referring to FIGS. 14A-14C, time-dependent thermal signatures for three different explosives are shown. In this illustration, the time-dependent thermal signatures are the time derivative of the temperature released over time from the area imaged by a particular pixel. However, as discussed above, in other examples, the time-dependent thermal signatures may be, for example, the time derivative of the radiant energy detected by a pixel, the radiant energy detected by a pixel over time, and/or the temperature over time. Also, the time-dependent thermal signatures of the explosives shown in FIGS. 14A-14C are shown as a function of frame number. However, frame number may be converted to time based upon the rate at which the frames are collected (e.g., 60 frames per second).

As seen by comparing FIGS. 14A-14C to each other, the characteristics of the time-dependent thermal signatures of the three explosives are different. For example, explosive A has a steeper exotherm 1410 and endotherm 1415 than the exotherm 1420 and endotherm 1425 of explosive B. In other words, explosive A releases heat more rapidly when it explodes as compared to Explosive B. Additionally, explosive A cools to the background once the explosion is over more rapidly than explosive B cools to the background. In another example, explosive C has an endotherm 1430 followed by an exotherm 1435 and an endotherm 1440. Thus, while the thermal signatures of explosives A, B, and C all have an exotherm followed by an endotherm (and would thus be detected by the coarse filter as explosives), the thermal signatures of explosives A, B, and C also have unique characteristics that may be used to further categorize, or even identify, the explosives. For example, explosive A may be classified as a plastic explosive. Once the time-dependent thermal signature associated with explosive A is detected and determined to be an explosive (based on the presence of an exotherm followed by an endotherm), the class of explosive may be determined based on the particular traits of the signature. For example, explosive A may be determined to be an explosive and further determined to have plastic explosive characteristics based on the rapid rise in temperature associated with explosive A's exotherm. Other characteristics of the thermal signatures may be used to classify the explosive. For example, the thermal signature characteristics may include the time duration and number of the endotherm and/or exotherm peaks, location of the peaks, the temperature at which thermal decomposition occurs, the duration of thermal decomposition, and the number of thermal decompositions.

In some implementations, the actual explosive itself may be identified in addition to classifying the explosive as a particular type of explosive. Continuing the example above, the particles may be identified as "explosive A." Classification or identification of explosives is generally done by comparing a detected time-dependent thermal signature to a known thermal signature. However, as discussed above, such a comparison is not necessarily performed to determine that some type of explosive is present. In some implementations, if the thermal signature does not match any of the known thermal signatures, the thermal signature is stored with the known thermal signatures such that it may be compared with thermal signatures detected subsequently.

Figure 15B:
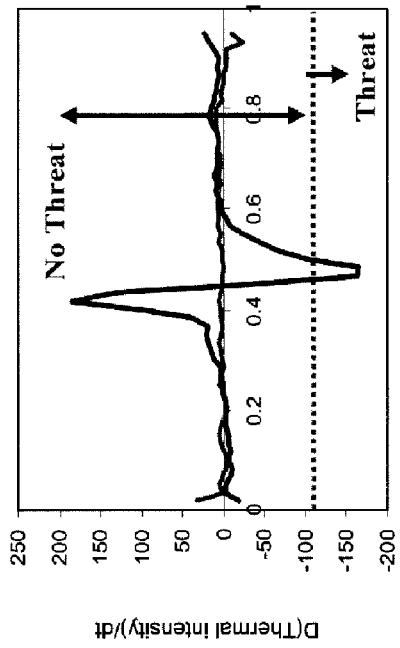
Figure 15C:
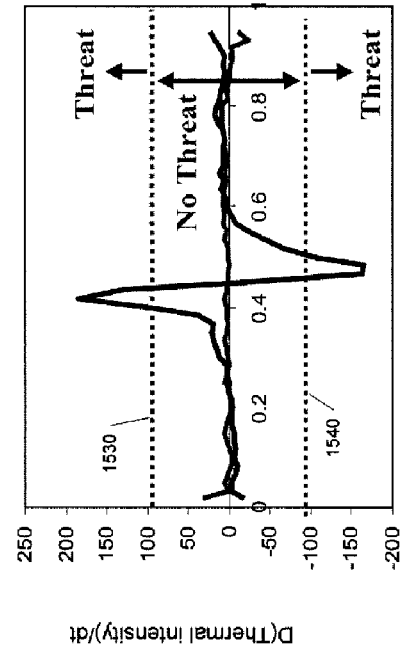
Figure 15A:
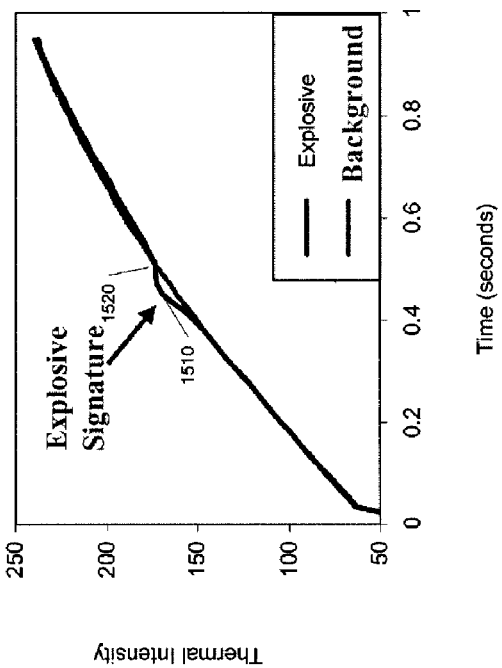

Referring to FIGS. 15A-15C, examples of using an exotherm and/or an endotherm to determine the presence of an explosive are shown. FIG. 15A shows an example of a time-dependent thermal signature of a pixel that images explosives and a pixel that does not. As discussed in the examples above, the thermal signature of the pixel that images explosives includes an exotherm 1510 and an endotherm 1520. Also as discussed above, the thermal signature may be the radiant energy detected by the pixel, or the thermal signature may be a temperature derived from the radiant energy. FIGS. 15B and 15C show a the time derivative of the thermal signature shown in FIG. 15A. In some implementations, such as the implementation shown in FIG. 15B a threshold is applied to the endotherm to determine whether or not an explosive is present. In other implementations, such as the implementation shown in FIG. 15C, a first threshold 1530 is applied to determine if there is an exotherm in the thermal signature and a second threshold 1540 to determine if there is an endotherm in the thermal signature. Thermal signatures that meet or exceed both the first threshold 1530 and the second threshold 1540 may be determined to be associated with explosives regardless of other characteristics that the time-dependent thermal signatures may have. The first threshold 1530 may be exceeded when the thermal signature has a value that is greater than or equal to the value of the first threshold 1530. The second threshold 1540 may be exceeded when the thermal signature has a value that is less than or equal to the value of the second threshold 1540. For example, the first threshold 1530 and the second threshold 1540 may be used to with the coarse filter discussed above with respect to FIG. 11 to determine whether explosives are present.

Figure 16:
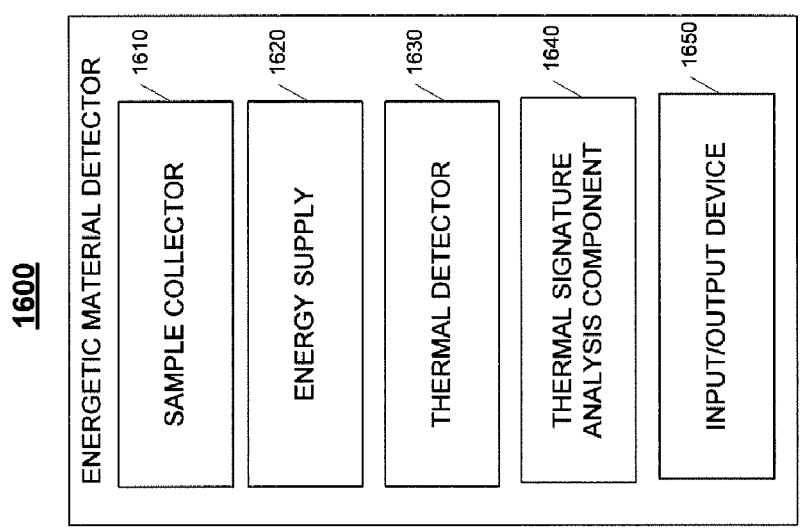
FIGS. 16, 17, 18A, and 18B are examples of systems for detecting energetic materials.

Referring to FIG. 16, an example system 1600 may be used to determine if explosives are present in a sample area. The example system 1600 includes a sample collector 1610, an energy supply 1620, a thermal detector 1630, a thermal signature analysis component 1640, and an input/output device 1650.

The sample collector 1610 may be a conductive material on which explosive samples may be collected or harvested. The sample collector 1610 may be, for example, foil. The energy supply 1620 supplies energy to the sample collector 1610 and any explosive samples present on the sample collector 1610. For example, the energy supply 1620 may supply sufficient activation energy to initiate thermal decomposition (e.g., an explosion) of samples present on the sample collector 1620. The energy supply may heat the sample collector 1620 to, for example, 300° C. in less than one second.

The thermal detector 1630 may be, for example, an infrared detector that detects radiant energy released from any samples on the sample collector 1620. The thermal detector 1630 may be one of the infrared detectors described above. In some implementations, the thermal detector 1630 may convert the detected radiant energy into temperature based on a predetermined calibration. The system 1600 also includes a thermal signature analysis component 1640, which may implement one or more processes configured to determine whether explosives are present on the sample collector 1620. For example, the process 1040 discussed above with respect to FIG. 11 may be implemented with the thermal signature analysis component 1640. The thermal signature analysis component 1640 generally includes a computer-readable medium configured to store instructions that, when executed, implement a process such as the process 1040. The thermal signature analysis component 1640 also includes a processor and a storage device.

The system 1600 also includes an input and output device 1650. The input and output device 1650 may include a receptacle for receiving the sample collector 1610, a printer, a touchscreen for selecting commands for the system 1600, and/or any other type of input/output device for communicating with the system 1600.

Figure 17:
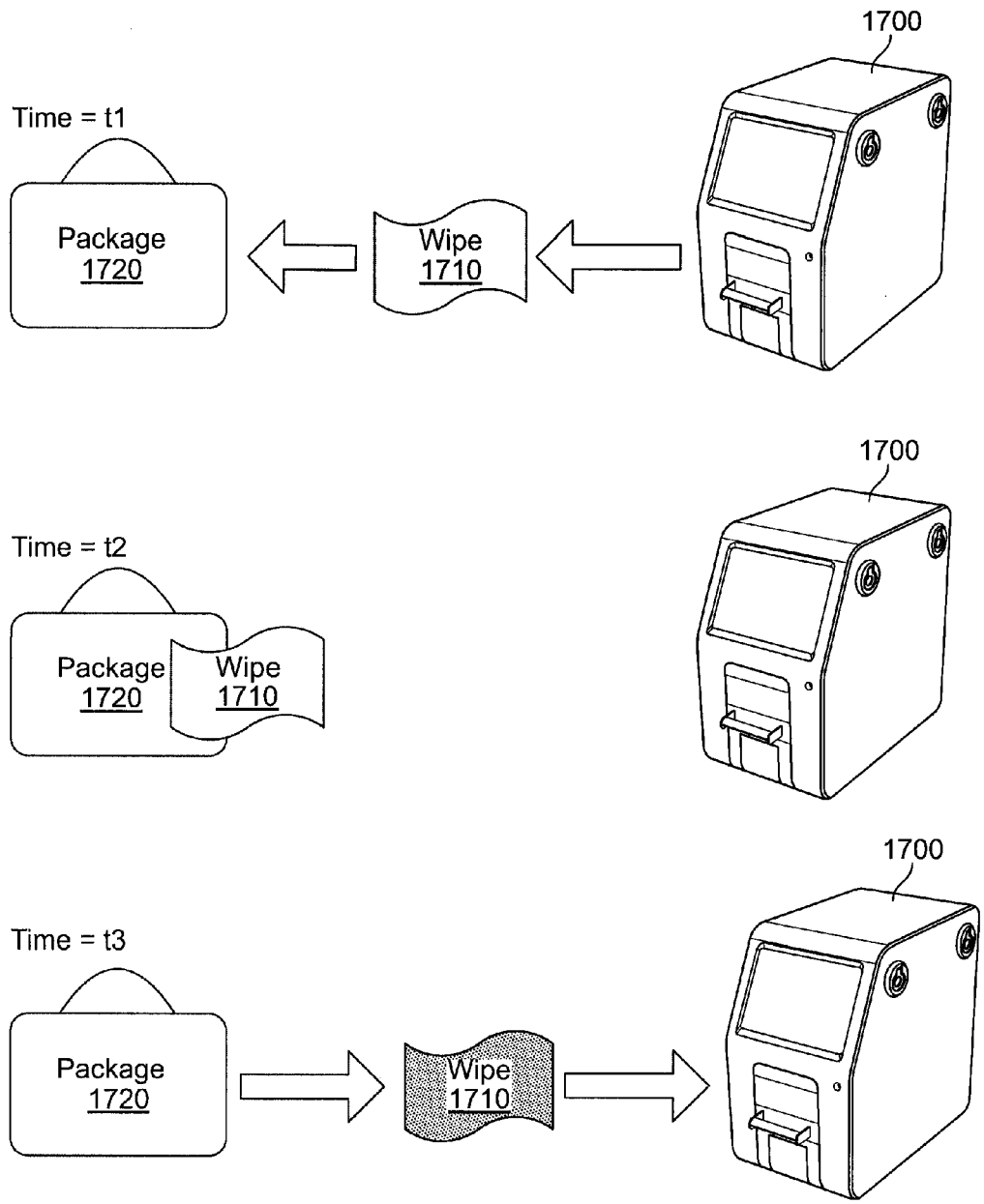

Referring to FIG. 17, a system such as the system 1600 described above may be implemented as a desktop system 1700 (which also may be referred to as a benchtop system) and used to determine whether a wipe 1710, which came into contact with a package 1720, includes explosives. After making contact with the surface of the package 1720, the wipe 1710 may include trace amounts of explosives. The presence of explosives on the wipe 1710 may indicate that the package 1720 is a suspicious package and that the package 1720 contains explosive materials or was handled by a person who had handled explosive materials. The desktop system 1700 generally includes the components 1610-1650 described above with respect to the system 1600. For example, the wipe 1710 may be the sample collector 1610.

The desktop system 1700 may be composed of commercially available components. For example, the desktop system 1700 may be operated on universal power (e.g., 110/220V, 50/60 Hz) with a maximum current draw of 10 A (110V) or 5 A (220V). Additionally, the desktop system may operate in environments where the temperature is 0-40° C. and the relative humidity is 0-95% (non-condensing). In some implementations, the desktop system 1700 may be sized for convenient transport. For example, the desktop system may be the shape and size of a desktop personal computer with dimensions of 18.3"H×11"W×20"D and weighing about 25 pounds.

In one example, the desktop system 1700 may be used as shown in FIG. 17. At time=t1, the wipe 1710 is removed from the desktop system 1700. At time=t2, the wipe 1710 makes contact with the package 1720 and collects trace amounts of explosives that may be present on the surface of the package 1720. At time=t3, the wipe 1720 is placed into the desktop system 1700 and analyzed as described above. After the wipe 1720 is analyzed, the desktop system 1700 may produce an indication of ALARM or PASS to indicate the presence or absence, respectively, of explosives on the wipe 1720. In some implementations, the desktop system 1700 may provide the ALARM or PASS indication within two seconds of inserting the wipe 1710 into the desktop system 1700.

In addition to providing an indication of the presence or absence of explosives, the desktop system also may provide a probability of detection and a false alarm rate.

Figure 18A:
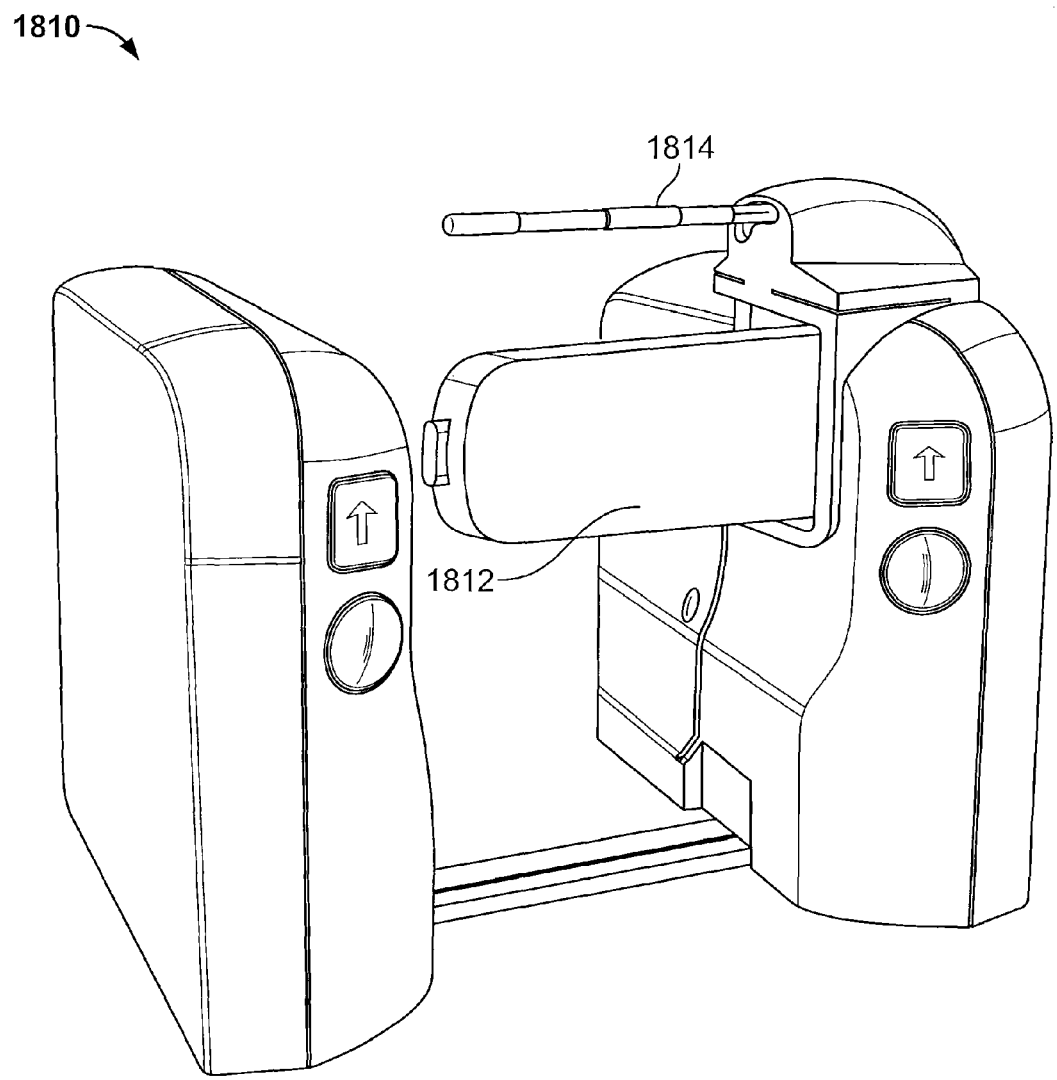
Figure 18B:
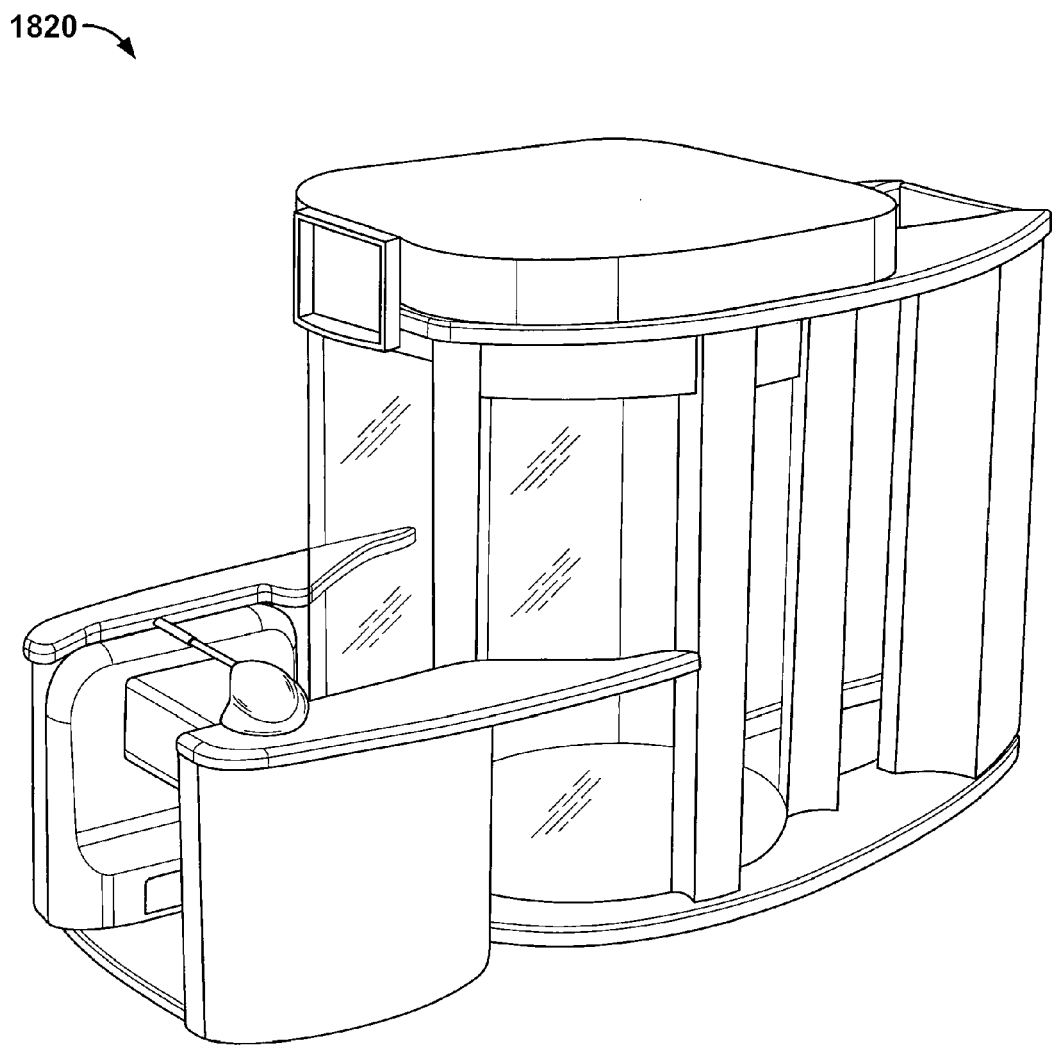

Referring to FIGS. 18A and 18B, the system 1600 may be implemented as a turnstile-based system 1810 or a checkpoint personnel screener 1820. Similar to the desktop system 1700 and the system 1600, the turnstile-based system 1810 and the checkpoint personnel screener 1820 may be used to determine the presence of trace amounts of explosives. For example, the turnstile-based system 1810 may detect traces of explosive materials present on persons that pass through the turnstile-based system 1810. In some implementations, the turnstile-based system 1810 may include an explosive sampling material on a gate 1812 through which persons pass through when walking through the turnstile-based system 1810. The turnstile-based system 1814 also may include other security devices, such as fingerprint scanner 1814. The checkpoint personnel screener 1820 similarly may detect trace amounts of explosives present on persons passing through the checkpoint personnel screener 1820.

It is understood that other modifications are within the scope of the claims.

What is claimed is:
1. A method of detecting explosive materials, the method comprising:
  energizing a sample area in an atmosphere that comprises ambient oxygen, the energizing being sufficient to initiate anaerobic decomposition of explosive particles;
  monitoring a thermal energy status of the sample area, the thermal energy status including at least one of a radiant energy and a temperature; and
  analyzing the thermal energy status of the sample area to determine whether explosive particles are included in a region included in the sample area.

2. The method of claim 1, wherein:
monitoring a thermal energy status of the sample area comprises monitoring the sample area with a thermal detector and detecting radiant energy released from the sample area, and
a region included in the sample area comprises a region imaged by a pixel of the thermal detector.

3. The method of claim 1, wherein monitoring a thermal energy status of the sample area includes monitoring at least one of radiant energy or temperature released from exothermic decomposition of particles.

4. The method of claim 1, wherein energizing the sample area includes resistively heating the sample area and applying a current through a conductive collection material.

5. The method of claim 4, wherein applying a current through a conductive collection material includes applying a current through a metal mesh.

6. The method of claim 4, wherein applying a current through a conductive collection material includes applying one or more of a step current and a ramp current.

7. The method of claim 1, wherein energizing the sample area includes radiatively heating the sample area.

8. The method of claim 7, wherein radiatively heating the sample area includes radiatively heating the sample area from a distance outside an area adjacent to the device used to radiatively heat the sample area.

9. The method of claim 7, wherein radiatively heating the sample area comprises radiatively heating the sample area using a laser or a lamp.

10. The method of claim 1, wherein energizing the sample area comprises heating the sample area at a rate between about 300° C./second and 400° C./second.

11. The method of claim 1, wherein monitoring the thermal energy status of the sample area comprises monitoring the thermal energy status of the region, and further comprising determining a thermal signature of the region included in the sample area based on the thermal energy status of the region.

12. The method of claim 11, wherein:
a value of the thermal signature includes an increase during a first time period and a decrease during a second time period, and
determining whether explosive particles are included in the region comprises determining whether the thermal signature includes the increase during the first time period and the decrease during the second time period.

13. The method of claim 12, wherein the first time period occurs before the second time period.

14. The method of claim 11, wherein determining the thermal signature of the region included in the sample area comprises determining the time rate of change of the thermal energy status of the region.

15. The method of claim 14, wherein determining the thermal signature of the region included in the sample area further comprises:
determining the average monitored thermal energy status of the sample area at a time, and
subtracting the average monitored thermal energy status at the time from the thermal energy status of the region before determining the time rate of change of the thermal energy status of the region.

16. The method of claim 11, wherein analyzing the thermal energy status to determine whether explosive particles are included in the region comprises determining that explosive particles are included in the region and further comprising:
determining one or more characteristics of the thermal signature;
comparing at least one of the one or more characteristics of the thermal signature to characteristics of known thermal signatures; and
classifying the thermal signature based on the comparison after determining that explosive particles are included in the region.

17. The method of claim 16, wherein determining one or more characteristics of the thermal signature includes analyzing the thermal signature to determine a heat of decomposition of the explosive particles.

18. The method of claim 16, wherein determining one or more characteristics of the thermal signature includes analyzing the thermal signature to determine an activation energy of the explosive particles.

19. The method of claim 16, wherein classifying the thermal signature based on the comparison comprises identifying the one or more explosive particles as a particular explosive material.

20. The method of claim 16, wherein classifying the thermal signature based on the comparison comprises identifying the one or more explosive particles as belonging to a class of explosive materials.

21. The method of claim 11, further comprising:
determining, based on the analyzed thermal energy status, that one or more explosive materials are included in the sample area;
comparing the thermal signature to known thermal signatures after determining that the sample area includes explosive materials;
determining whether the known thermal signatures includes the thermal signature; and
if a determination is made that the known thermal signatures do not include the thermal signature, storing the thermal signature as one of the known thermal signatures.

22. The method of claim 11, wherein analyzing the thermal energy status to determine whether explosive particles are included in the region comprises:
determining one or more characteristics of the thermal signature;
comparing at least one of the one or more characteristics of the thermal signature to characteristics of known thermal signatures; and
classifying the thermal signature based on the comparison.

23. A system for detecting explosive materials, the system comprising:
a sample energizer configured to energize a sample area in an atmosphere that comprises ambient oxygen, the sample energizer configured to produce energy sufficient to initiate anaerobic decomposition of an explosive particle;
a sensor configured to monitor a thermal energy status of the sample area, the thermal energy status including at least one of a radiant energy and a temperature; and
an electronic processor configured to:
determine the presence of explosive particles based on the thermal energy status of the region.

24. The system of claim 23, wherein monitoring the thermal energy status of the sample area comprises monitoring the thermal energy status of the region, and the processor is further configured to determine a thermal signature of the region included in the sample area, the determination being based on the thermal energy status of the region.

25. The system of claim 24, wherein:
a value of the thermal signature includes an increase during a first time period and a decrease during a second time period, and the analyzing device is configured to determine the presence of explosive particles based on characteristics of the thermal signature by determining whether the thermal signature includes the increase during the first time period and the decrease in the thermal energy status during the second time period.

26. The system of claim 24, wherein determining the thermal signature of a region included in the sample area comprises determining the time rate of change of the thermal energy status of the region.

27. The system of claim 24, wherein the electronic processor is further configured to:
   determine, based on the analyzed thermal signature, that one or more explosive materials are included in the sample area;
   determine one or more characteristics of the thermal signature;
   compare characteristics of the thermal signature to a library of characteristics of known thermal signatures; and
   classify the thermal signature based on the comparison.

28. A computer program product tangibly embodied on a computer-readable medium, the computer program product including instructions that, when executed, cause a thermal signature analysis component to perform operations comprising:
   energizing a sample area in an atmosphere that comprises ambient oxygen, the energizing being sufficient to initiate anaerobic decomposition of an explosive particle;
   monitoring a thermal energy status of the sample area, the thermal energy status including at least one of a radiant energy and a temperature; and
   analyzing the thermal energy status of the sample area to determine whether explosive particles are included in the region.

29. The method of claim 14, further comprising:
   applying a filter to data representing the time rate of change of the thermal energy status of the region; and
   identifying an endotherm and an exotherm in the filtered data.

30. A method of detecting explosive materials, the method comprising:
   energizing a sample area;
   monitoring a thermal energy status of the sample area, the thermal energy status including at least one of a radiant energy and a temperature;
   determining a thermal signature of a region included in the sample area based on a thermal energy status of the region; and
   analyzing the thermal signature to determine whether explosive particles are included in the region,
   wherein energizing the sample area includes radiatively heating the sample area.

31. The method of claim 30, wherein radiatively heating the sample area includes radiatively heating the sample area from a distance outside an area adjacent to the device used to radiatively heat the sample area.

32. The method of claim 30, wherein radiatively heating the sample area comprising radiatively heating the sample area using a laser.

33. The system of claim 23, wherein the sample area comprises at least a portion of a reusable collection material that is configured to hold particles, and further comprising:
   a housing defining an opening configured to receive the reuseable collection material that is configured to hold particles.

34. The system of claim 33, wherein the electronic processor is further configured to:
   determine a thermal signature of a region included in the sample area based on the monitored thermal energy status.

* * * * *